(12) United States Patent
Dinarello et al.

(10) Patent No.: US 7,279,155 B2
(45) Date of Patent: Oct. 9, 2007

(54) METHOD OF TREATMENT USING A CYTOKINE ABLE TO BIND IL-18BP TO INHIBIT THE ACTIVITY OF A SECOND CYTOKINE

(75) Inventors: Charles A. Dinarello, Boulder, CO (US); Soo-Hyun Kim, Aurora, CO (US); Philip Bufler, Graefelfing (DE)

(73) Assignee: Ares Trading S.A., Aubonne (CH)

( * ) Notice: Subject to any disclaimer, the term of this patent is extended or adjusted under 35 U.S.C. 154(b) by 319 days.

(21) Appl. No.: 10/679,201

(22) Filed: Oct. 3, 2003

(65) Prior Publication Data

US 2004/0120923 A1 Jun. 24, 2004

Related U.S. Application Data

(60) Provisional application No. 60/416,827, filed on Oct. 8, 2002.

(51) Int. Cl.
*A61K 38/19* (2006.01)
*A61K 38/17* (2006.01)

(52) U.S. Cl. .................. 424/85.2; 425/85.1; 514/12

(58) Field of Classification Search ............... None
See application file for complete search history.

(56) References Cited

U.S. PATENT DOCUMENTS

| | | | |
|---|---|---|---|
| 5,194,596 A * | 3/1993 | Tischer et al. | 530/399 |
| 5,350,836 A * | 9/1994 | Kopchick et al. | 530/399 |
| 5,945,310 A | 8/1999 | Young et al. | |
| 6,342,371 B1 * | 1/2002 | McDonnell et al. | 435/69.1 |

FOREIGN PATENT DOCUMENTS

| | | | |
|---|---|---|---|
| WO | WO99/37772 A1 | 7/1999 | |
| WO | WO 01/40247 A1 | 6/2001 | |
| WO | WO 0140247 A1 * | 6/2001 | |

OTHER PUBLICATIONS

Vukicevic et al., 1996, PNAS USA 93:9021-9026.*
Massague, 1987, Cell 49:437-8.*
Pilbeam et al., 1993, Bone 14:717-720.*
Skolnick et al., 2000, Trends in Biotech. 18:34-39.*
Bork, 2000, Genome Research 10:398-400.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Bowie et al, 1990, Science 247:1306-1310.*
Wells, 1990, Biochemistry 29:8509-8517.*
Thomson et al., Eds. The Cytokine Handbook, vol. 2, Fourth Edition, Academic Press, San Diego, CA. 2003, pp. 653-656, 740-741.*
Arthritis Foundation, Disease Center, Feb. 7, 2007.*
Pan et al., Cytokine Jan. 7, 2001 13(1):1-7.*
Kumar et al., Cytokine Apr. 21, 2002 18(2):61-71.*
NCBI accession No. AF200496, accessed May 9, 2006.*
Benjamin et al., 1998, Development 125:1591-1598.*
English translation of Kashiwamura, S. et al.; Nippon Rinsho; 56(7): 1798-1806 (1998).
Azam, T. et al.; The Journal of Immunology; 171:6574-6580 (2003).
Barton, J.L. et al.; Eur. J. Immunol.; 30:3299-3308 (2000).
Born, T.L. et al.; The Journal of Biological Chemistry; 273(45):29445-29450 (1998).
Busfield, S.J. et al.; Genomics; 66:213-216 (2000).
Corbaz, A. et al.; The Journal of Immunology; 168:3608-3616 (2002).
Debets, R. et al.; The Journal of Immunology; 167:1440-1446 (2001).
Dinarello, C.A.; Eur. Cytokine Netw.; 11:483-486 (2000).
Dinarello, C.A.; Blood, 87(6):2095-2147 (1996).
Gracie, J.A. et al.; J. Clin. Invest.; 104:1393-1401 (1999).
Kim, S.H. et al.; The Journal of Immunology; 166:148-154 (2001).
Kim, S.H. et al.; PNAS; 97(3):1190-1195 (2000).
Kumar, S. et al.; The Journal of Biological Chemistry; 275(14):10308-10314 (2000).
Kumar, S. et al.; Cytokine; 18(2):61-71 (2002).
Lin, H. et al.; The Journal of Biological Chemistry; 276(23):20597-20602 (2001).
Mallat, Z. et al.; Cir. Res.; 91:441-448 (2002).
Monteleone, G. et al.; The Journal of Immunology; 163:143-147 (1999).
Mulero, J.J. et al.; Biochemical and Biophysical Research Communications; 263:702-706 (1999).
Nakanishi, K. et al.; Annu. Rev. Immunol.; 19:423-474 (2001).
Novick, D. et al.; Immunity; 10:127-136 (1999).
Novick, D. et al., Cytokine, 14:334-342 (2001).
Ohta, Y. et al.; Arch. Derm. Res.; 293(7):334-42 (2001).
Okamoto, I. et al.; The Journal of Immunology; 162:3202-3211 (1999).
Olee, T. et al.; The Journal of Immunology; 162:1096-1100 (1999).
Pan, G. et al.; Cytokine, 13(1):1-7 (2001).
Pizarro, T.T. et al.; The Journal of Immunology; 162:6829-6835 (1999).
Puren, A.J. et al.; PNAS, 96:2256-2261 (1999).
Raeburn, C.D. et al.; Am. J. Physiol. Heart Circ. Physiol.; 283:H650-H657 (2002).
Saha, N. et al.; Arthritis & Rheumatism; 42(8):1577-1587 (1999).
Smith, D.E. et al.; The Journal of Biological Chemistry; 275(2)1169-1175 (2000).

(Continued)

*Primary Examiner*—Gary B. Nickol
*Assistant Examiner*—Cherie Woodward
(74) *Attorney, Agent, or Firm*—Nixon Peabody LLP

(57) ABSTRACT

The present invention relates to the use of a cytokine-1, preferably from the IL-1 family more preferably IL-1F7b, or an isoform, mutein, fused protein, functional derivative or fragment thereof, capable of binding to IL-18BP or a mutein, fused protein, functional derivative or fragment thereof and capable of inhibiting a receptor of a cytokine-2, cytokine-2 being a member of the IL-1 family, preferably IL-18, in the manufacture of a medicament for the treatment or prevention of a disease which is caused or aggravated by inducing said receptor of cytokine-2.

3 Claims, 6 Drawing Sheets

OTHER PUBLICATIONS

Taylor, S.L. et al.; Genomics; 79(5):726-733 (2002).
Torigoe, K. et al.; The Journal of Biological Chemistry; 272(41):25737-25742 (1997).
Urushihara, N. et al.; Journal of Pediatric Surgery; 35(3):446-449 (2000).
Vigers, G.P.A. et al.; Nature; 386:190-194 (1997).
Xiang, Y. et al.; Proc. Natl. Acad. Sci. USA; 96:11537-11542 (1999).
Yatsiv, I. et al.; Journal of Cerebral Blood Flow & Metabolism; 22:971-978 (2002).
Yu, S. et al.; Journal of Neuropathology and Experimental Neurology; 61(7):614-622 (2002).
Zecchina, G. et al.; Journal of Hematotherapy & Stem Cell Research; 10:769-776 (2001).
Bufler, et al., "A complex of the IL-1 homologue IL-1F7b and IL-18 binding protein reduces IL-18 activity," *PNAS*, vol. 99, No. 21: pp. 13723-13728, Oct. 15, 2002.

* cited by examiner

```
huIL-18    MAAEPVEDNCINFVAMKFIDNT-LYFIAED---DEN---LESDYFGKLE---S--K
           :          .::.      .:. . .::    ::     ::.   . ::    :
huIL-1F7b  M----------SFVG----ENSGVKMGSEDWEKDEPQCCLEDPAVSPLEPGPSLPA huIL-18    LS-V-----IRNLN-------DQ---VLFIDQGN-----------RP-LF----EDM
           .. :      ..:::       ::    ::  .:.::            :: .:    ..
huIL-1F7b  MNFVHTSPKVKNLNPKKFSIHDQDHKVLVLDSGNLIAVPDKNYIRPEIFFALASSL huIL-18    TDSDCRDNAPRTIFI-IS-----MY--KD---SQPRGMAVTISVKCEKISTLSCEN
           ....  ..:  :.. .:       .:   ::    :.:       ....: ::.  :. .
huIL-1F7b  SSASAEKGSP--ILLGVSKGEFCLYCDKDKGQSHP-----SLQLKKEKLMKLAAQhuIL-18    KIISFKEMNPPDNIKDTKSDIIFFQRSVPGHDNKMQFESSSYEGYFL--ACE-KE-
                  ::       ...  .::..  .: :   : ! .::...  :.:.    .: .:
huIL-1F7b  -----KE--------SARRPFIFYRAQV-GSWN-M-LESAAHPGWPICTSCNCNEP huIL-18    ---RDLFKLILKKEDELGDRSIMPTVQ---------NE--D
             : :      :.,    . : :. :               .: :
huIL-1F7b  VGVTDKF------ENR---KHIEPSFQPVCKAEMSPSEVSD
```

Figure 1

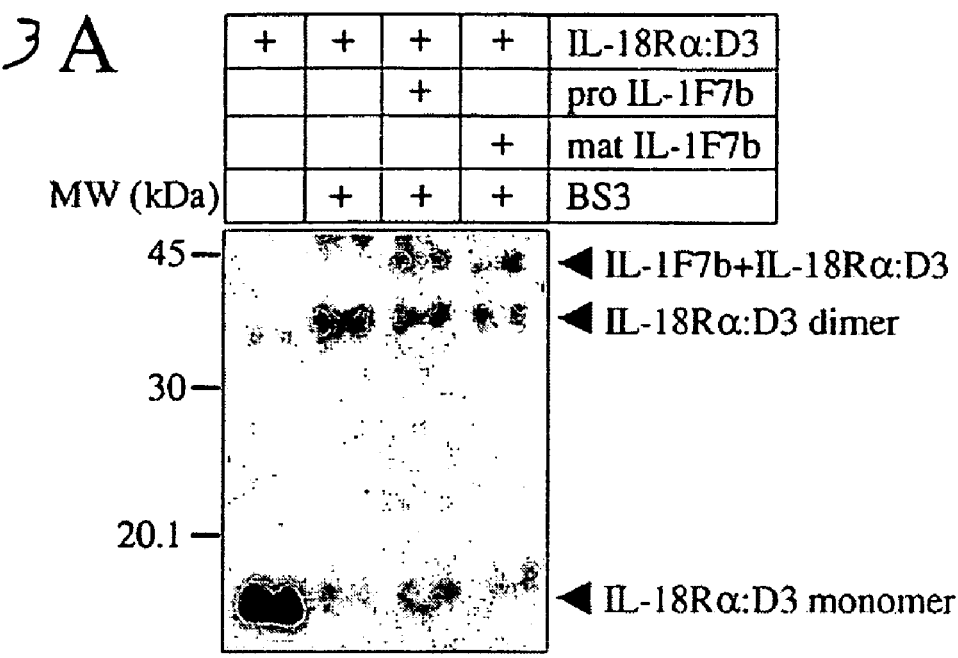
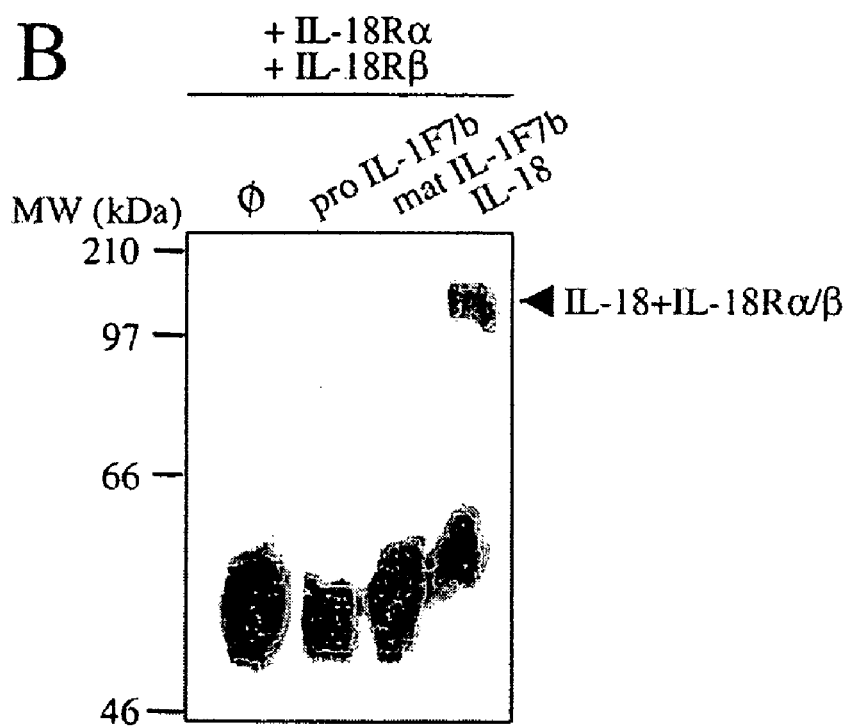
Figure 3

METHOD OF TREATMENT USING A CYTOKINE ABLE TO BIND IL-18BP TO INHIBIT THE ACTIVITY OF A SECOND CYTOKINE

FIELD OF THE INVENTION

The invention relates to a method of using a cytokine, capable of binding IL-18 binding protein, to inhibit the activity of a second cytokine, the second cytokine being a member of the IL-1 family.

BACKGROUND OF THE INVENTION

In 1989, an endotoxin-induced serum activity that induced interferon-γ (IFN-γ) obtained from mouse spleen cells was described (Nakamura et al 1989). This serum activity did not function as a direct inducer of IFN-γ but rather as a co-stimulant together with IL-12, IFN-α/β, TNF or mitogens. An attempt to purify the activity from post-endotoxin mouse serum revealed an apparently homogeneous 50-55 kDa protein (Nakamura et al. 1993). Since other cytokines can act as co-stimulants for IFN-γ production, the failure of neutralizing antibodies to IL-1, IL-4, IL-5, IL-6, or TNF to neutralize the serum activity suggested it was a distinct factor. In 1995, the same scientists demonstrated that the endotoxin-induced co-stimulant for IFN-γ production was present in extracts of livers from mice preconditioned with *P. acnes* (Okamura at al. 1995). In this model, the hepatic macrophage population (Kupffer cells) expands and in these mice, a low dose of bacterial lipopolysaccharide (LPS), which in non-preconditioned mice is not lethal, becomes lethal. The factor, named IFN-γ-inducing factor (IGIF) and later designated interleukin-18 (IL-18), was purified to homogeneity from 1,200 grams of *P. acnes*-treated mouse livers. Degenerate oligonucleotides derived from amino acid sequences of purified IL-18 were used to clone a murine IL-18 cDNA (Okamura et al. 1995). Messenger RNAs for IL-18 and interleukin-12 (IL-12) are readily detected in activated macrophages. IL-18 does not induce IFN-γ by itself, but functions primarily as a co-stimulant with mitogens or IL-12. The human cDNA sequence for IL-18 was reported in 1996.

Interleukin IL-18 shares structural features with the IL-1 family of proteins (Nakamura et al. 1993, Okamura et. al 1995, Ushio et al. 1996 and Bazan et al. 1996). Unlike most other cytokines, which exhibit a four-helix bundle structure, IL-18 and IL-1β have an all β-pleated sheet structure (Tsutsui et al. 1996). Similarly to IL-1β, IL-18 is synthesized as a biologically inactive precursor (proIL-18), lacking a signal peptide (Ushio et al 1996). The IL-1β and IL-18 precursors are cleaved by caspase-1 (IL-1β-converting enzyme, or ICE), which cleaves the precursors after an aspartic acid residue in the P1 position. The resulting mature cytokines are readily released from the cell (Ghayur et al. 1997 and Gu et al. 1997).

IL-18 is a co-stimulant for cytokine production (IFN-γ, IL-2 and granulocyte-macrophage colony stimulating factor) by T helper type I (Th1) cells (Kohno et al. 1997) and also a co-stimulant for FAS ligand-mediated cytotoxicity of murine natural killer cell clones (Tsutsui et al. 1996).

Th1 lymphocytes are involved in the immune responses against tumors (Seki et al. 2000). Th1 responses include the secretion of the cytokines IL-2, IL-12, IL-18 and IFN-γ, as well as the generation of specific cytotoxic T lymphocytes recognizing specific tumor antigens. The Th1 response is also a vital arm of host defense against many microorganisms. However, the Th1 response can also be associated with non-desirable effects, such as the development of several autoimmune diseases, inflammation and organ transplant rejection.

Cytokine binding proteins (soluble cytokine receptors) are usually the extracellular ligand binding domains of their respective cell surface cytokine receptors. They are produced either by alternative splicing or by proteolytic cleavage of the cell surface receptor. These soluble receptors have been described in the past: for example, the soluble receptors of IL-6 and IFN-γ (Novick et al. 1989), TNF (Engelmann et al. 1989 and Engelmann et al. 1990), IL-1 and IL-4 (Maliszewski et al. 1990), IFN-α/β (Novick et al. 1994, Novick et al. 1992). One cytokine-binding protein, named osteoprotegerin (OPG, also known as osteoclast inhibitory factor—OCIF), a member of the TNFR/Fas family, appears to be the first example of a soluble receptor that exists only as a secreted protein (Anderson et al. 1997, Simonet et al. 1997, Yasuda et al. 1998).

An interleukin-18 binding protein (IL-18BP) was affinity purified, on an IL-18 column, from urine (Novick et al. 1999). IL-18BP abolishes IL-18 induction of IFN-γ and of IL-8, activation of NF-kB in vitro and induction of IFN-γ in vivo. IL-18BP is a soluble circulating protein, which is constitutively expressed in the spleen, and belongs to the immunoglobulin superfamily. The most abundant IL-18BP isoform, the spliced variant isoform a, exhibits a high affinity for IL-18 with a rapid on-rate and a slow off-rate, and a dissociation constant (Kd) of approximately 400 pM (Kim et al. 1999).

The residues involved in the interaction of IL-18 with IL-18BP have been described through the use of computer modelling (Kim et al. 1999) and based on the interaction of IL-1β with the IL1R type I (Vigers et al. 1997). In the model for IL-18 binding to the IL-18BP, the Glu (E) residue at position 42 and the Lys (K) residue at position 89 of IL-18 have been proposed to bind to Lys-130 and Glu-114 in IL-18BP, respectively (Kim et al. 1999).

IL-18BP is constitutively present in many cells (Puren et al. 1999) and circulates in healthy humans (Urushihara et al. 2000). The high affinity of IL-18BP to IL-18 as well as the high concentration of IL-18BP found in the circulation (20 fold molar excess over IL-18) represents a unique situation in cytokine biology. Therefore, it is presumed that most, if not all, of the IL-18 molecules in the circulation is bound to the IL-18BP. The circulating IL-18BP, which competes with cell surface receptors for IL-18, may act as a natural anti-inflammatory and an immunosuppressive molecule.

Viral agents encode IL-18BP like proteins, for example *M. contagiosum* viral proteins MC53 and MC54 share a significant homology to mammalian IL-18BP (Novick et al. 1999). *M. contagiosum* proteins MC53 and MC54 possess the ability to bind and neutralize human IL-18 in a fashion similar to that of IL-18BP (Xiang and Moss 1999). The ectromelia poxvirus p13 protein, which is homologous to IL-18BP, binds human IL-18 and inhibits its activity in vitro. Mice infected with a p13 deletion mutant virus exhibited decreased levels of infectivity (Born et al. 2000). Therefore, infectivity degree seems to correlate with the presence of viral IL-18BP.

The high levels of circulating IL18BP may represent a natural defense against excessive Th1 responses to infection and development of autoimmune diseases.

The cytokines of the IL-1-family, including IL-18, possess a variety of inflammatory and immunoregulatory properties during the first line and secondary response to infection (Dinarello 1996 and Nakanishi 2001). Six new members of the interleukin-1 (IL-1) gene family have been discovered from expressed sequence tag data base searches (Barton 2000, Busfield 2000, Debets 2001, Kumar 2000, Lin 2001, Mulero 1999, Pan 2001 and Smith 2000). These proteins share a common β-barrel pattern consisting of 12.beta.-strands and significant amino acid homology with the IL-1 receptor antagonist (IL-1Ra), IL-1β and IL-18. These new members of the IL-1 family are derived from a common ancestor as are IL-1 and IL-18 (Nicklin 2002, Taylor 2002). Except for IL-18, each maps to the same region on human chromosome 2 (Nicklin 2002, Mulero 2000, Taylor 2002 and Busfield 2000). Their biological function of these IL-1 homologues is presently unknown. Five different splice variants of the novel IL-1 homologue IL-1H4 (IL-IF7a-e) have been described (Busfield 2000, Kumar 2000, Pan 2001, Smith 2000, Taylor 2002). The first isoform described, IL-1F7a, has an unique N-terminus consisting of exon 3 of the IL-1 F7 gene, which is not present in the other splice variants of the gene. The short isoforms IL-IF7c, IL-IF7d and IL-IF7e lack exon 4,2 or both, respectively. Only IL-1F7b and c containing exon 1 and 2 express a N-terminal prodomain that has a potential caspase-1 (ICE) cleavage site(s) (Kumar 2002). In addition to these splice variants, amino acid polymorphisms (V31 G and A42T) exist in IL-1F7b based on two base pair mutations in exon 2 (Kumar 2000, Pan 2001). Despite extensive data base searches and sequencing of the IL-1-gene locus, no murine homologue of IL-1 H4 has yet been found. IL-1F7b shares significant sequence homology with IL-18. The hallmark for IL-18 activity is its ability to induce IFNγ in T-cells or natural killer (NK) cells in the presence of IL-2, IL-12 or IL-15 as costimulant. The activity of IL-18 is mediated via the IL-18R complex consisting of the ligand-binding chain termed IL-18R.alpha. (Torigoe 1997) and a signaling chain termed IL-18β (3 (Born 1998, Kim 2001). Upon binding to the IL-18Rα chain and formation of the hetero complex with the IL-18Rβ chain, IL-18 induces activation of IL-1 receptor-associated kinase and TNF receptor-associated factor 6 (TRAF-6). These activated kinases eventually result in the translocation of nuclear factor .kappa.-B (NF-κB) (Matsumoto, Robinson). IL-1F7b has been reported to bind to the IL-18R.alpha. using a receptor pulldown assay (Pan 2001) or computerchip-based binding studies (BIACORE®) (Mulero 2000). Significant but low affinity binding of Kd=130 mM was only observed for the mature form of IL-1F7b without the propeptide suggesting biological relevance to IL-1F7b processing by ICE (Kumar 2002). Despite the binding to the IL-18Rα, no IL-18-like or antagonistic activity of either pro or mature IL-1F7b was demonstrated (Pan 2001, Kumar 2002).

It has been suggested that interleukin IL-18 is involved in the progression of pathogenicity in chronic inflammatory diseases, including endotoxin shock, hepatitis, and autoimmune-diabetes (Kahiwamura and Okamura, 1998). A further indication of a possible role of IL-18 in the development of liver injury resulted from experiments published by Tsuij et al. (Tsuij et al., 1999), showing an elevated level of IL-18 in lipopolysaccharide-induced acute liver injury in a mouse model. However, the mechanism of the multi-functional factor IL-18 in the development of liver injury has not been elucidated so far.

Liver damage or injury may have diverse causes. It may be due to viral or bacterial infections, alcohol abuse, immunological disorders, or cancer, for example.

Viral hepatitis, due to Hepatitis B virus and Hepatitis C virus, for example, are poorly managed diseases that afflict large number of people world-wide. The number of known hepatitis viruses known is constantly increasing. Apart from Hepatitis B and C virus, at least four other viruses causing virus-associated hepatitis have been discovered so far, called Hepatitis A, D, E and G-Virus.

Alcoholic liver disease is another widespread disease associated with chronic consumption of alcohol. Immune hepatitis is a rare autoimmune disease that is poorly managed. Liver injury also includes damages of the bile ducts. Primary biliary cirrhosis (PBC) is an autoimmune liver disease characterized by destruction of the intrahepatic bile ducts.

Several studies have demonstrated that damage to the liver in diseases such as alcoholic hepatitis, liver cirrhosis, viral hepatitis and primary biliary cirrhosis is associated with T-helper cell-1 (Th1) responses. In one study, a novel liver injury model was established in mice by targeting of ovalbumin-containing liposomes into the liver, followed by adoptive transfer of ovalbumin-specific Th1 cells. Combined treatment of mice with ovalbumin-containing liposomes and Th1 cell transfer caused an increase in serum transaminase activity that was paralleled with an elevation of serum IFN-γ levels. In sharp contrast, ovalbumin-specific Th2 cell transfer resulted in an increase of serum IL-4 levels but did not induce liver injury. The liver injury was blocked by anti-IFN-γ antibodies and anti-tumor necrosis factor (TNF)-α antibodies. These findings indicate that Th1 cells are the major effector cells in acute liver injury (Nishimura and Ohta, 1999) In another set of studies it was shown that mice over-expressing IFN-γ exhibit spontaneous hepatitis without any pathogen or any other stimulant (Okamoto et al., 1998).

Another study implicated Th1 responses in primary biliary cirrhosis (PBC). PBC is an autoimmune liver disease characterized by destruction of the intrahepatic bile ducts. It is generally believed that cellular immune mechanisms, particularly involving T cells, result in this bile duct damage. The relative strength of Th1 and Th2 responses has recently been proposed to be an important factor in the pathophysiology of various autoimmune diseases. In this study, the subset balance in PBC was evaluated by detection of cytokines specific to the two T-cell subsets, i.e., IFN-γ for Th1 cells and IL-4 for Th2 cells. IFN-γ and IL-4 messenger RNA (mRNA) positive cells were counted in liver sections from 18 patients with PBC and 35 disease controls including chronic active hepatitis C, extrahepatic biliary obstruction, and normal liver, using nonisotopic in situ hybridization and immunohistochemistry. Mononuclear cells expressing IFN-γ and IL-4 mRNA were aggregated in inflamed portal tracts in PBC livers, but were rarely present in extrahepatic biliary obstruction, alcoholic fibrosis, or normal liver sections. The IFN-γ and IL-4 mRNA positive cells in PBC livers were detected in significantly higher numbers than in control livers (P<0,01). Moreover, IFN-γ mRNA expression was more commonly detected than IL-4 expression in PBC livers, and the levels of IFN-γ mRNA expression were highly correlated with the degree of portal inflammatory activity. IFN-γ mRNA-positive cells were detected primarily around damaged bile ducts that were surrounded by lymphoid aggregates. The data indicate that Th1 cells are the more prominent T-cell subset in the lymphoid infiltrates in PBC (Harada et al., 1997).

The cytokine pattern on viral antigen recognition is also believed to exert a profound influence on the resolution of viral infections and viral clearance. One study investigated whether a cytokine imbalance oriented toward Th2 type response plays a role in chronic hepatitis B. Cytokine profiles of peripheral blood mononuclear cells associated with chronic hepatitis B were analyzed by RT-PCR. Upon hepatitis B surface antigen (HbsAg) stimulation, expression of IFN-γ, IL-2, IL-4, and IL-10 was detected in 41%, 8%, 41%, and 50% of the patients, respectively. Among these cytokines, the expression of the Th1 cytokine IFN-γ was associated with high levels of serum AST/ALT (Aspartate aminotransferase/Alanine aminotransferase), representing typical markers of liver damage. Th2 type cytokines were not shown to exert a protective effect on hepatocytes. In conclusion, production of a Th1 cytokine, IFN-γ, by HBsAg-reactive cells was associated with hepatocyte damage in chronic hepatitis B (Lee et al., 1999). High levels of the FAS ligand and its receptor (CD95) were reported in liver of hepatitis B patients (Luo et al., 1997). FAS ligand is considered to be one of the major cytotoxic agents leading to hepatocyte apoptosis.

Another study identified factors associated with the progression of liver injury in 30 hepatitis C virus/RNA (HCV/RNA)-positive untreated patients with chronic hepatitis. Necroinflammatory and architectural damage were evaluated using Ishak's score. Activated hepatic stellate cells (HSC) were visualized by immunohistochemistry for α-smooth muscle actin (αSMA) and quantitated by morphometry. Plasma HCV/RNA was evaluated using a competitive RT-PCR method. To study the type of immune response involved in the progression of liver injury, IFN-γ-positive cells (as expression of a Th1-like response) were evaluated by immunohistochemistry and quantitated by morphometry. It was found that HSC were mostly detected close to areas of lobular necroinflammation or lining fibrotic septa. The αSMA- and Sirius Red-positive parenchyma correlated significantly with necroinflammatory and architectural scores. IFNγ-positive cells were detected in periportal areas associated with the inflammatory infiltrates and significantly correlated with architectural damage. It was therefore concluded that HSC activation and progression of liver injury are associated with a Th1-like response (Baroni et al, 1999). Similarly to the case of Hepatitis B, FAS ligand and its receptor were found in liver and sera of hepatitis C patients (Hiramatsu et al, 1994; Okazaki et al, 1996; Lio et al., 1998)

Th1 cytokines and other Th1 markers were found to be associated with alcoholic hepatitis and liver cirrhosis. Inflammatory stimuli and lipid peroxidation activate nuclear factor κB (NF-κB) and upregulate proinflammatory cytokines and chemokines. In one study, the relationship between pathological liver injury, endotoxemia, lipid peroxidation, and NF-κB activation and imbalance between pro- and anti-inflammatory cytokines was evaluated. Rats (5 per group) were fed ethanol and a diet containing saturated fat, palm oil, corn oil, or fish oil by intragastric infusion. Dextrose isocalorically replaced ethanol in control rats. Pathological analysis was performed and measurements of endotoxin were taken, lipid peroxidation, NF-κB, and messenger RNA (mRNA) levels of proinflammatory cytokines (TNFα, IL-1beta, IFN-γ, and IL-12), C-C chemokines (regulated upon activation, normal T cell expressed and secreted [RANTES], monocyte chemotactic protein [MCP]-1, macrophage inflammatory protein [MIP]-1-α), C—X—C chemokines (cytokine induced neutrophil chemoattractant [CINC], MIP-2, IP-10, and epithelial neutrophil activating protein [ENA]-78), and anti-inflammatory cytokines (IL-10, IL-4, and IL-13). Activation of NF-κB and increased expression of proinflammatory cytokines C—C and C—X—C chemokines was seen in the rats exhibiting necroinflammatory injury (fish oil-ethanol and corn oil-ethanol). These groups also had the highest levels of endotoxin and lipid peroxidation. Levels of IL-10 and IL-4 mRNA were lower in the group exhibiting inflammatory liver injury. Thus, activation of NF-κB occurs in the presence of proinflammatory stimuli and results in increased expression of Th1 proinflammatory cytokines and chemokines (Naji et al., 1999). FAS ligand and its receptor are also elevated in alcoholic liver diseases, suggesting once again that Th1 cytokines are involved in the autoimmune processes induced in alcoholic hepatitis (Galle et al., 1995; Taieb et al, 1998; Fiore et al., 1999).

TNF-α has also emerged as a common pathway in the pathogenesis of alcohol-related hepatic necro-inflammation. Increased levels of hepatic and serum TNF have been documented in animal models of alcoholic liver disease and in human alcoholic liver disease. This dysregulated TNF metabolism has been postulated to play a role in many of the metabolic complications and the liver injury of alcoholic liver disease (Grove et al., 1997; McClain and Cohen, 1989). For instance it was found in one study that patients with alcoholic hepatitis had higher TNF-α levels (mean, 26.3 ng/L; 95% CI, 21.7 to 30.9) than normal subjects (6.4 ng/L; CI, 5.4 to 7.4). Patients who subsequently died had a higher TNF-α level (34.7 ng/L; CI, 27.8 to 41.6) than survivors (16.6 ng/L; CI, 14.0 to 19.2). In patients with alcoholic hepatitis, TNF-α levels correlated positively with serum bilirubin (r=0.74; P=0.0009) and serum creatinine (r=0.81; P=0.0003). Patients with alcoholic hepatitis had higher TNF-α levels than patients with inactive alcoholic cirrhosis (11.1 ng/L; CI, 8.9 to 13.3) and severely alcoholic persons without liver disease (6.4 ng/L; CI, 5.0 to 7.8). Patients with abnormal renal function had lower TNF-α levels (14.1 ng/L; CI, 5.4 to 22.8) than patients with alcoholic hepatitis. It was therefore concluded that elevations in TNF-α in alcoholic hepatitis are most marked in severe cases, suggesting that TNF-α plays a role in the pathogenesis (Bird et al., 1990).

TNF mediates many of the biologic actions of endotoxin. Recent studies have shown that TNF administration may cause liver injury and that TNF may mediate the lethality of the hepatotoxin galactosamine. One of the most potent TNF inducers is endotoxin. Because patients with alcoholic liver disease frequently have endotoxemia and because many of the clinical manifestations of alcoholic hepatitis are known biologic actions of TNF, its activity was evaluated in patients with alcoholic hepatitis. Basal and lipopolysaccharide-stimulated TNF release from peripheral blood monocytes, a major source of TNF production, was determined in 16 patients with alcoholic hepatitis and 16 healthy volunteers. Eight of 16 alcoholic hepatitis patients and only two of 16 healthy volunteers had detectable spontaneous TNF activity (p less than 0.05). After lipopolysaccharide stimulation, mean monocyte TNF release from alcoholic hepatitis patients was significantly increased to over twice that of healthy controls (25.3+/−3.7 vs. 10.9+/−2.4 units per ml, p less than 0.005). It was therefore concluded that monocytes from alcoholic hepatitis patients have significantly increased spontaneous and lipopolysaccharide-stimulated TNF release compared to monocytes from healthy volunteers (McClain and Cohen, 1989.

Lipopolysaccharide (LPS)-binding protein (LBP) and CD14 play key intermediary roles in the activation of cells by endotoxin. Gut-derived LPS has been postulated to participate in promoting pathological liver injury in alcoholic liver disease. It was demonstrated that rats fed intragastrically with ethanol in oil for 4 weeks had elevated levels of CD14 and LBP in their Kupffer cells and hepatocytes, respectively. Expression of CD14 mRNA was also elevated in nonmyeloid cells. Enhanced LBP and CD14 expression rapidly increases the LPS-induced expression of various pro-inflammatory cytokines and correlates with the presence of pathological liver injury in alcoholic liver injury (Su et al., 1998; Lukkari et al., 1999).

Arthritis is a disease involving joint inflammation. The joints show swelling, stiffness, tenderness, redness or warmth. The symptoms may be accompanied by weight loss, fever or weakness. When these symptoms last for more than two weeks, inflammatory arthritis e.g. rheumatoid arthritis may be the cause. Joint inflammation may also be caused by infection, which can lead to septic arthritis. A very common type of arthritis is degenerative joint disease (osteoarthritis).

The medicaments commonly prescribed for arthritis and related conditions are non-steroidal anti-inflammatory drugs (NSAIDs). NSAIDs include aspirin and aspirin-like drugs. They reduce inflammation, which is the cause for joint pain, stiffness and swelling of the joints. However, NSAIDs are unspecific drugs having a number of side effects, involving bleeding of the stomach (Homepage of the Department of Orthopaedics of the University of Washington on Arthritis, Frederick Matsen (Chairman), www.orthop.washington.edu). In addition to NSAIDs, Celebrex™, a cyclooxygenase (COX-2) inhibitor, is used to relieve the signs and symptoms of osteoarthritis and rheumatoid arthritis in adults. It is also indicated for the treatment of patients with familial adenomatous polyposis.

WO 01/00229 describes a combination of tumors necrosis factor (TNF) antagonists and COX-2 inhibitors for the treatment of inflammation.

TNF antagonists are also used for the treatment of arthritis. TNF antagonists are described, for example, in WO 9103553.

Studies indicate that the interleukin IL-18 plays a proinflammatory role in joint metabolism. Olee et al. (1999) showed that IL-18 is produced by articular chondrocytes and induces proinflammatory and catabolic responses. The IL-18 MRNA was induced by IL-1β in chondrocytes. Chondrocytes produced the IL-18 precursor and in response to IL-1 stimulation secreted the mature form of IL-18. Studies on IL-18 effects on chondrocytes further showed that it inhibits TGF-β-induced proliferation and enhances nitric oxide production. IL-18 stimulated the expression of several genes in normal human articular chondrocytes including inducible nitric oxide synthase, inducible cyclooxygenase, IL-6, and stromelysin. Gene expression was associated with the synthesis of the corresponding proteins. Treatment of normal human articular cartilage with IL-18 increased the release of glycosaminoglycans. These finding identified IL-18 as a cytokine that regulates chondrocyte responses and contributes to cartilage degradation.

The localisation of Interleukin-1β-converting enzyme (ICE)/caspase-1 in human osteoarthritic tissues and its role in the maturation of interleukin-1beta and interleukin-18 have been shown by Saha et al. (1999). Saha et al. studied the expression and production of caspase-1 in human normal and osteoarthritic (OA) cartilage and synovium, quantitated the level of ICE in OA chondrocytes, and examined the relationship between the topographic distribution of ICE, interleukin-1β (IL-1β), and IL-18, as well as apoptosis of chondrocytes. The experiments performed in this study indicated that ICE was expressed and synthesised in both human synovial membrane and cartilage, with a significantly greater number of cells staining positive in OA tissue than in normal tissue. ICE production was preferentially located in the superficial and upper intermediate layers of articular cartilage. The production of mature IL-1beta in OA cartilage explants and chondrocytes was completely blocked by treatment with a specific ICE inhibitor, which also markedly diminished the number of IL-18-positive cells. The relationship between active IL-1beta and ICE suggests that ICE may promote OA progression by activating this proinflammatory cytokine, and that IL-18 may play a role in cartilage pathology.

Gracie et al. (1999) suggested a proinflammatory role for IL-18 in rheumatoid arthritis. Gracie et al. detected the IL-18 mRNA and protein within rheumatoid arthritis synovial tissues in significantly higher levels than in osteoarthritis controls. It was also shown that a combination of IL-12 or IL-15 with IL-18 induced the IFN-γ production by synovial tissues in vitro. Furthermore, IL-18 administration of collagen/inclomplete Freund's adjuvant-immunized mice facilitated the development of an erosive, inflammatory arthritis, suggesting that IL-18 may be proinflammatory in vivo.

However, so far, apart from chemical compounds, only the blockade of TNFα and IL-1β by using soluble receptors or monoclonal antibodies have been shown to decrease murine collagen-induced arthritis (CIA, which is a mouse model for rheumatoid arthritis) (Williams et al., 1994), and were therefore suggested as a therapeutic for rheumatoid arthritis.

The term "chronic or idiopathic inflammatory bowel diseases" embraces at least two conditions: Crohn's disease and ulcerative colitis. Both are diseases of the gastrointestinal tract, Crohn's disease most commonly affecting the small bowel. When it also involves the colon, the differential diagnosis from ulcerative colitis (see below) can be a problem.

The chronic inflammation and ulceration in Crohn's disease usually starts with either small-intestinal obstruction or abdominal pain which may mimic acute appendicitis; other presentations can relate to its complications. The course of the disease is chronic, and there may be exacerbations and remissions in spite of therapy. Onset is usually in early adult life, with about half of all cases beginning between the ages of 20 and 30 years and 90% between 10 and 40 years. Slightly more males than females are affected.

Microscopy reflects the gross appearances. Inflammation involvement is discontinuous: it is focal or patchy. Collections of lymphocytes and plasma cells are found mainly in the mucosa and submucosa but usually affecting all layers (transmural inflammation). The classical microscopic feature of Crohn's disease is the presence of granule cells surrounded by a cuff of lymphocytes. The incidence of idiopathic inflammatory bowel diseases shows considerable geographic variation. These diseases have a much higher incidence in northern Europe and the United States than in countries of southern Europe, Africa, South America and Asia, although increasing urbanisation and prosperity is leading to a higher incidence in parts of southern Europe and Japan (General and Systematic Pathology, Churchill Livingstone, $3^{rd}$ edition 2000, JCE Underwood, Ed.).

In Crohn's disease, clinically there are two main groups, the first comprising patients whose disease goes into lasting remission within three years of onset, the second comprising patients with disease persisting beyond three years.

Whatever the aetiology, there is evidence of persistence and inappropriate T-cell and macrophage activation in Crohn's disease with increased production of pro-inflammatory cytokines, in particular interleukins (IL) 1, 2, 6 and 8, Interferon (IFN)-γ and Tumor Necrosis Factor (TNF) α. Crohn's disease is characterised by sustained (chronic) inflammation accompanied by fibrosis. The process of fibroblastic proliferation and collagen deposition may be mediated by transforming growth factor β, which has certain anti-inflammatory actions, namely fibroblast recruitment, matrix synthesis and down-regulation of inflammatory cells, but it is likely that many other mediators will be implicated.

Ulcerative colitis is a non-specific inflammatory disorder of the large intestine, usually beginning in the rectum and extending proximately to a varying extent. Unlike Crohn's disease, ulcerative colitis is confined to the large intestine.

There is growing evidence to indicate that ulcerative colitis is a consequence of altered autoimmune reactivity but mucosal injury could also result from inappropriate T-cell activation and indirect damage brought about by cytokines, proteases and reactive oxygen metabolites from macrophages and neutrophils. This latter mechanism of damage to the colonic epithelium has been termed "innocent bystander" injury. Evidence in favour of autoimmunity is the presence of self-reactive T-lymphocytes and auto-antibodies directed against colonic epithelial cells and endothelial cells, and anti-neutrophil cytoplasmic auto-antibodies (ANCA). However, ulcerative colitis should not be thought of as an autoimmune disease in which mucosal injury is a direct consequence of an immunological reaction to self-antigens (General and Systematic Pathology, supra).

With regard to the therapy of Crohn's disease, most people are first treated with drugs containing mesalamine, a substance that helps control inflammation. Patients who do not benefit from it or who cannot tolerate it may be put on other mesalamine-containing drugs, generally known as 5-ASA agents. Possible side effects of mesalamine preparations include nausea, vomiting, heartburn, diarrhea, and headache.

Some patients take corticosteroids to control inflammation. These drugs are the most effective for active Crohn's disease, but they can cause serious side effects, including greater susceptibility to infection.

Drugs that suppress the immune system are also used to treat Crohn's disease. Most commonly prescribed are 6-mercaptopurine and a related drug, azathioprine. Immunosuppressive agents work by blocking the immune reaction that contributes to inflammation. These drugs may cause side effects like nausea, vomiting, and diarrhea and may lower a person's resistance to infection. When patients are treated with a combination of corticosteroids and immunosuppressive drugs, the dose of corticosteroids can eventually be lowered. Some studies suggest that immunosuppressive drugs may enhance the effectiveness of corticosteroids.

The U.S. Food and Drug Administration has approved the drug infliximab for the treatment of moderate to severe Crohn's disease that does not respond to standard therapies (mesalamine substances, corticosteroids, immunosuppressive agents) and for the treatment of open, draining fistulas. Infliximab, the first treatment approved specifically for Crohn's disease, is an anti-tumor necrosis factor (TNF) monoclonal antibody. Anti-TNF removes TNF from the bloodstream before it reaches the intestines, thereby preventing inflammation.

Antibiotics are used to treat bacterial overgrowth in the small intestine caused by stricture, fistulas, or prior surgery. For this common problem, the doctor may prescribe one or more of the following antibiotics: ampicillin, sulfonamide, cephalosporin, tetracycline, or metronidazole.

Diarrhea and crampy abdominal pain are often relieved when the inflammation subsides, but additional medication may also be necessary. Several anti-diarrheal agents could be used, including diphenoxylate, loperamide, and codeine. Patients who are dehydrated because of diarrhea are usually treated with fluids and electrolytes.

There remains to be a need for effective therapy for the treatment and/or prevention of inflammatory bowel diseases, in particular Crohn's disease (CD) and ulcerative colitis (UC), which have reduced side effects or are ideally even free of side effects.

Both histological and immunological observations indicate that cell-mediated immunity and T cell activation are key features of CD. Studies from humans and experimental models suggest that, in CD, the local immune response tends to be predominantly Th1 in type (Desreumaux et al, 1997) and that locally released cytokines, such as IFN-γ, IL-1β, and TNF-α, contribute to promote and expand the inflammatory response (Reimund et al, 1996).

The cytokine IL-18 plays an important role in Th1 mediated immune response in collaboration with the cytokine IL-12 by stimulating IFN-γ secretion, enhancing natural killer cell cytotoxicity, and stimulating TH1 cell differentiation (Uschito et al, 1996).

IL-18 acts together with IL-12, IL-2, antigens, mitogens, and possibly further factors, to induce the production of IFN-γ. IL-18 also enhances the production of GM-CSF and IL-2, potentiates anti-CD3 induced T cell proliferation, and increases Fas-mediated killing of natural killer cells. Mature IL-18 is produced from its precursor by the IL-1β converting enzyme (ICE, caspase-1). The IL-18 receptor consists of at least two components, co-operating in ligand binding. High- and low-affinity binding sites for IL-18 were found in murine IL-12 stimulated T cells (Okamoto et al., 1998), suggesting a multiple chain receptor complex. Two receptor subunits have been identified so far, both belonging to the IL-1 receptor family (Okamoto et al., 1999). The signal transduction of IL-18 involves activation of NF-κB (Matsumoto et al, 1997).

Recently, IL-18 has been suggested to have some implication in Inflammatory Bowel Diseases (Pizarro et al, 1999; Monteleone et al, 1999).

Pizarro et al. (1999) characterised the expression and localisation of IL-18 in colonic specimens and isolated mucosal cell populations from patients with Crohn's disease. Using a semiquantitative RT-PCR protocol, IL-18 mRNA transcripts were found to be increased in freshly isolated intestinal epithelial cells and lamina propria mononuclear cells from CD compared with ulcerative colitis and noninflamed control patients. IL-18 mRNA transcripts were more abundant in intestinal epithelial cells compared with lamina propria mononuclear cells. Immunohistochemical analysis of surgically resected colonic tissues localised IL-18 to both lamina propria mononuclear cells (specifically, macrophages and dendritic cells) as well as intestinal epithelial cells. Western blot analysis revealed that an 18,3-kDa band, consistent with both recombinant and mature human IL-18 protein, was found predominantly in CD vs UC intestinal mucosal biopsies; a second band of 24 kDa, consistent with the inactive IL-18 precursor, was detected in non inflamed areas from both CD and UC biopsies and was the sole form found in noninflamed controls.

Monteleone et al. (1999) confirmed these findings. Whole mucosal intestinal tissue and lamina propria mononuclear cells of 12 Crohn's disease and 9 ulcerative colitis patients and 15 non-inflammatory bowel disease controls were tested for IL-18 by semiquantitative RT-PCR and Western blot analysis. Transcripts for IL-18 were found in all samples tested. However, increased IL-18 mRNA accumulation was detected in both mucosal and lamina propria mononuclear cells samples from Crohn's disease in comparison to ulcerative colitis and controls. In Crohn's disease, transcripts for IL-18 were more abundant in the mucosal samples taken from involved areas. An 18-kDa band consistent with mature IL-18 was predominantly found in Crohn's disease mucosal samples. In mucosal samples from non-IBD controls, IL-18 was present as the 24-kDa polypeptide. Consistently, active IL-1beta-converting enzyme (ICE) subunit (p20) was expressed in samples from either CD or UC, whereas, in colonic mucosa from non-IBD controls, ICE was synthesised as precursor (p45) only.

Ohta et al. 2001 showed that the expression of IL-18 was increased in psoriatic lesional skin relative to that in normal skin. Their findings indicate that keratinocyte-derived IL-18 participates in the development of the Th1 response in psoriatic lesions, and that its bioactivity appears to be tightly regulated in cutaneous inflammation.

In several animal models, antibodies that neutralize endogenous IL-18 reduce the severity of disease. Endotoxin lethality is prevented by anti-IL-18. Even in models that are interferon-γ independent, neutralization of IL-18 prolongs survival. Anti-IL-18 also protects the liver against cellular injury induced by toxins or activated T cells. In models of hepatic melanoma metastasis, IL-18 blockade reduces the adherence of malignant cells by preventing IL-18 upregulation of vascular endothelial adhesion-1 molecule expression. IL-18 and IL-12 act synergistically to stimulate I cells and natural killer cells to produce IFN-gamma but neutralization of IL-18 prevents IL-12 induction of IFN-gamma. IL-18, like several cytokines, can be used to enhance host defense against tumors in mice a mechanism that is most often IFN-gamma-dependent. Nevertheless, it is the proinflammatory portfolio of IL-18, which likely contributes to enhance host defenses. In models or arthritis, lung injury or inflammatory bowel disease, neutralization of IL-18 reveals the important role of this cytokine in mediating inflammation (Dinarello 2000).

Published data imply that IL-18 may play a phatological role in inflammatory CNS diseases. Neutralization of IL-18 was shown to protect from brain injury (Yatsiv et al. 2002), ischemic injury (Mallat et al. 2002), cardiac dysfunction (Raeburn 2002) and neuritis (Yu et al 2002) in animal models.

However, there is evidence that IL-18 promotes host defense against tumors in mice. For example, in syngeneic mice, murine mammary carcinoma cells expressing murine IL-12 or murine IL-18 were less tumorogenic and formed tumors more slowly than did control non-expressing cells (Coughlin et al. 1998). Antibody neutralization studies revealed that the antitumor effects required IFN-γ. In a study by Tasaki it has been observed protective immunity induced in murine colon carcinoma cells by the expression of interleukin-18. Colon cancer cells transduced with vectors encoding the IL-18 gene could not form subcutaneous tumors when introduced in immunocompetent mice, and became resistant to non-transduced inoculated colon cancer cells. Immunohistochemical analysis revealed that the numbers of blood vessels in colon tumors with cells transduced with IL-18 vectors were markedly reduced. The loss of tumorigenicity of colon IL-18 transduced cells was not observed in immunocompromised mice. Thus, the IL-18 secreted from tumor cells acts as an adjuvant since it stimulates T helper type 1 cells to induce antitumor response (Tasaki et al 2000).

It has been suggested that IFN-α, exerts its anti-inflammatory action in vivo in chronic hepatitis C patients inter alia by induction of IL-18BP (Kaser et al. 2002).

In previous work it was found that compared with healthy individuals, the levels of the IL-18BP are markedly elevated in many diseases such as in sepsis (Novick 2001) in Acute Graft versus Host Disease (Zecchina 2001), in Crohn's disease (Corbaz 2002). However it has been found also that in these patients the levels of IL-18 in the circulation are very high and therefore the levels of IL-18BP present in the circulation may not be sufficient for complete neutralization of IL-18.

Thus, is therefore a need to provide means to treat and/or prevent diseases in which a cytokine from the IL-1 family such as IL-18 is involved in their pathology.

SUMMARY OF THE INVENTION

The present invention relates to the use of a cytokine-1, preferably from the IL-1 family, more preferably IL-1F7b, or an isoform, mutein, fused protein, functional derivative or fragment thereof, capable of binding to IL-18BP or a mutein, fused protein, functional derivative or fragment thereof and capable of inhibiting a receptor of a cytokine-2, cytokine-2 being a member of the IL-1 family, preferably IL-18, in the treatment or prevention of a disease which is caused, aggravated, or enhanced by inducing said receptor of cytokine-2.

More specifically, cytokine-1 inhibits cytokine-2 activity by binding to the signalling chain of the receptor of cytokine-2. Thus, cytokine-1 may be employed for the treatment or prevention of inflammatory diseases, selected from endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis or for the treatment or prevention of metastasis formation. If desired, IL-18BP or a mutein, fused protein, functional derivative or fragment thereof, can further be administered.

Instead of the cytokine-1 protein, a vector encoding such cytokine-1 can be used in the treatment or prevention of a disease which is caused, aggravated, or enhanced by inducing said receptor of cytokine-2.

The above protein(s) and/or vectors according to the invention can be administered systemically, subcutaneous and/or intramuscularly.

In addition, the invention provides use of a vector for endogenous gene activation of a cytokine-1, preferably from the IL-1 family, more preferably IL-1F7b capable of binding to IL-18BP or a mutein, fused protein, functional derivative or fragment thereof and capable of inhibiting a receptor of a cytokine-2, cytokine-2 being a member of the IL-1 family, preferably IL-18, in the treatment or prevention of a disease which is caused, aggravated or enhanced by inducing said receptor of cytokine-2. More specifically, cytokine-1 inhibits cytokine-2 activity by binding to the. signalling chain of the receptor of cytokine-2.

More specifically the invention relates the use of a cyokine-1 for treatment or prevention of inflammatory diseases, such as endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis, or for the treatment or prevention of metastasis formation. If desired, according to the invention IL-18BP or a mutein, fused protein, functional derivative or fragment thereof can further be administered.

The vector for endogenous gene activation according to the invention can be administered systemically, subcutaneous and/or intramuscularly.

In another aspect, the invention provides the use of an inhibitor of a cytokine-1, preferably of the IL-1 family, more preferably IL-1F7b, or an isoform, mutein, fused protein, functional derivative or fragment thereof, capable of binding to IL-18BP or an isoform, a mutein, fused protein, or fragment thereof and capable of inhibiting a receptor of a cytokine-2, cytokine-2 being a member of the IL-1 family, preferably IL-18, for the treatment or prevention of a disease which is caused or enhanced by cytokine-2 receptor inhibition. More specifically, the invention relates to the use of an inhibitor of a cytokine-1 according to the invention for the treatment or prevention of a viral disease or for the treatment or prevention of cancer.

Preferred cytokine-1 inhibitors include, for example, antibodies, antisense nucleic acid, RNAi, or soluble cytokine-2 receptor or a fragment thereof capable of binding the cytokine-1.

In addition, the invention provides a method of inhibiting a receptor of a cytokine-2, cytokine-2 being a member of the IL-1 family, preferably IL-18 in a patient in need comprising administration of a therapeutically effective amount of cytokine-1 to bind to the cytokine-2 receptor. The cytokine-1 is preferably IL-F7b or an isoform, a mutein, fused protein, or fragment thereof able to bind IL-18BP or an isoform, a mutein, fused protein, or fragment thereof. More specifically, cytokine-1 inhibits cytokine-2 activity by binding to the signalling chain of the receptor of cytokine-2. The invention is useful in the treatment or prevention of inflammatory diseases, selected from endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis or for the treatment or prevention of metastasis formation. If desired, IL-18BP or a mutein, fused protein, functional derivative or fragment thereof can be co-administered with cytokine-1. Cytokine-1 according to the method of invention, can be administered systemically, subcutaneous and/or intramuscularly.

Alternatively, the method of the invention comprise administration of vectors encoding said cytokine-1.

In addition, the invention provides a method for inhibiting a receptor of a cytokine-2, cytokine-2 being a member of the IL-1 family, preferably IL-18 in a patient in need comprising administration of a therapeutically effective amount of a vector for gene activation of cytokine-1, preferably IL-F7b or an isoform, a mutein, fused protein, or fragment thereof able to bind IL-18BP or an isoform, a mutein, fused protein, or fragment thereof. More specifically, cytokine-1 inhibits cytokine-2 activity by binding to the signalling chain of the receptor of cytokine-2. A cyokine-1 may be employed for treatment or prevention of inflammatory diseases, such as endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis or for the treatment or prevention of metastasis formation. If desired, IL-18BP or a mutein, fused protein, functional derivative or fragment thereof can be co-administered with cytokine-1. A vector for gene activation according to the method of invention, can be administered systemically, subcutaneous and/or intramuscularly.

In another aspect, the invention relates to a method for treating or preventing a disease caused or enhanced by cytokine-2 receptor inhibition in a patent in need thereof. The method comprises administering an effective amount of a cytokine-1 inhibitor to induce the cytokine-2 receptor. The cytokine-1 is preferably from the IL-1 family, more preferably IL-1F7b, or an isoform, mutein, fused protein, functional derivative or fragment thereof, capable of binding to IL-18BP or an isoform, a mutein, fused protein, or fragment thereof. The cytokine-2 is a member of the IL-1 family, preferably IL-18. More specifically, the method of the invention comprises an inhibitor of cytokine-1 for the prevention or treatment or prevention of a viral disease or for the treatment or prevention of cancer.

BRIEF DESCRIPTION OF THE FIGURES

FIG. 1 Sequence Similarity of Human IL-18 (SEQ ID NO:5) and IL-IF7b (SEQ ID NO: 6).

Human IL-18 (accession no. D49950) and human IL-IF7b (accession no. AF200496) are shown. Alignment was generated using Expert Protein Analysis System (EXPASY®) with additional manual adjustment. The amino acid identity of IL-18 with IL-IF7b is 28% and the similarity 55%. The underlined amino acids represent the ICE-cleavage site in IL-18 and the predicted cleavage site in IL-IF7b.

Figure 2:
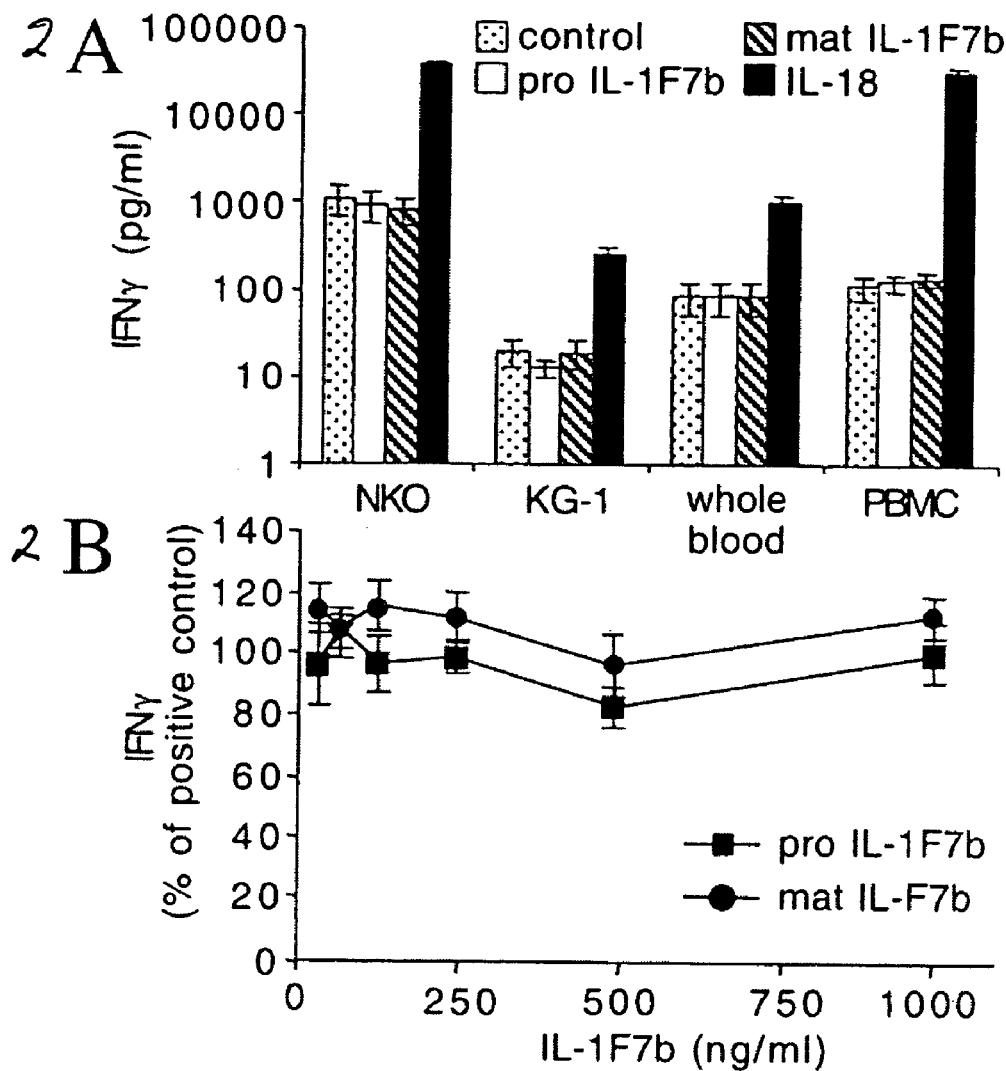

FIG. 2 Shows That IL-IF7b Neither Stimulates Nor Inhibits IFNγ Production Induced by IL-18.

FIG. 2A Human NKO cells, cultures of whole human blood, PBMC (costimulated with IL-12 (1 ng/ml)) and KG-1 cells (costimulated with TNFα. (10 ng/ml)), were treated with 100 ng/ml of recombinant IL-IF7b (pro or mature form) or IL-18. After 18 hrs (48 hrs for KG-1) IFNγ was measured in the supernatant. Results are shown as mean+/−SEM of three independent experiments.

FIG. 2B Induction NK cells by IL-18 (20 ng/ml) in the presence of IL-12 (1 ng/ml) and increasing concentrations of pro or mature IL-IF7b. The data represent mean+/−SEM of three independent experiments.

FIGS. 3A and 3B Show Cross-Linking of IL-IF7b and IL-18Ra-Extracellular Domain 3

FIG. 3A Reducing SDS-PAGE of IL-IF7b cross-linked to IL-18Ra: D3. After blotting on nitrocellulose the cross-linked proteins were visualized by a monoclonal mAb against the IL-18Rα.

FIG. 3B Formation of a ternary complex of the IL-18Rα- and β-ECD in the presence of IL-18 but not IL-IF7b after chemical cross-linking. After Western blotting the complexes were visualized by an anti-his$_6$ tag monoclonal antibody against the his$_6$-tagged IL-18Rβ.

Figure 4:
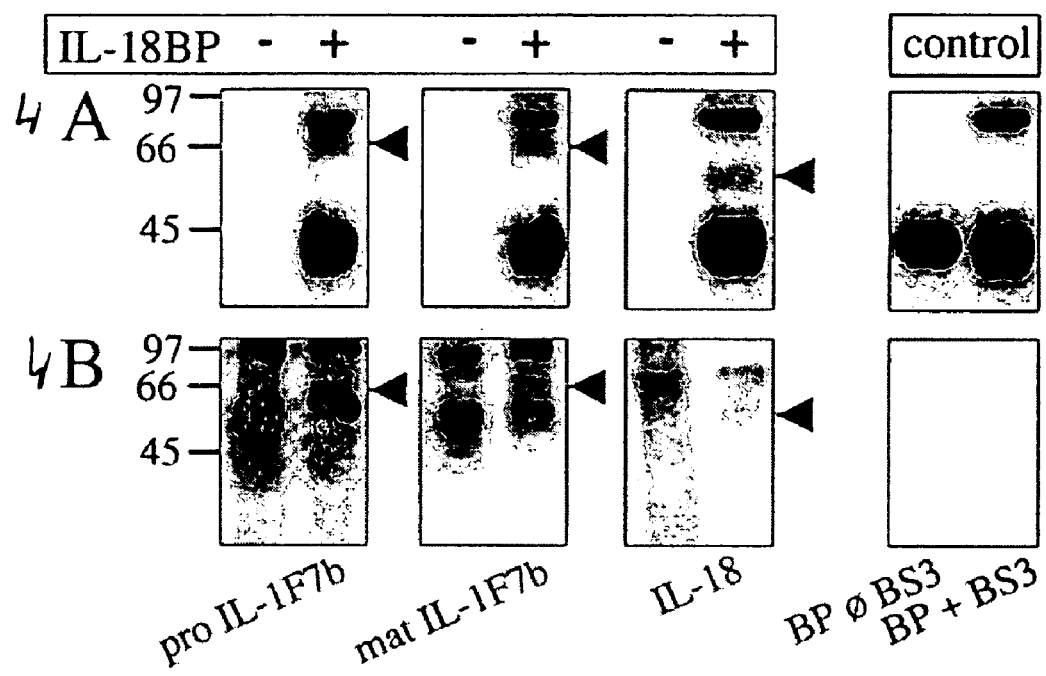

FIGS. 4A and 4B show Cross-Linking of IL-IF7b and IL-18BP

FIG. 4A Detection of cross-linked proteins (1.5 μg each) on Western blot using a rabbit anti-IL-18BP serum.

FIG. 4B Immunoprecipitation of cross-linked proteins (10 μg each) with a mAb against IL-18BP. Cross-linked IL-1F7b/IL-18BP and the control lanes (IL-18BP+/−BS3, the cross linking agent) were stained with a rabbit anti-IL-1F7b serum. IL-18/IL-18BP complex was detected with rabbit anti-IL-18 serum.

Figure 5:
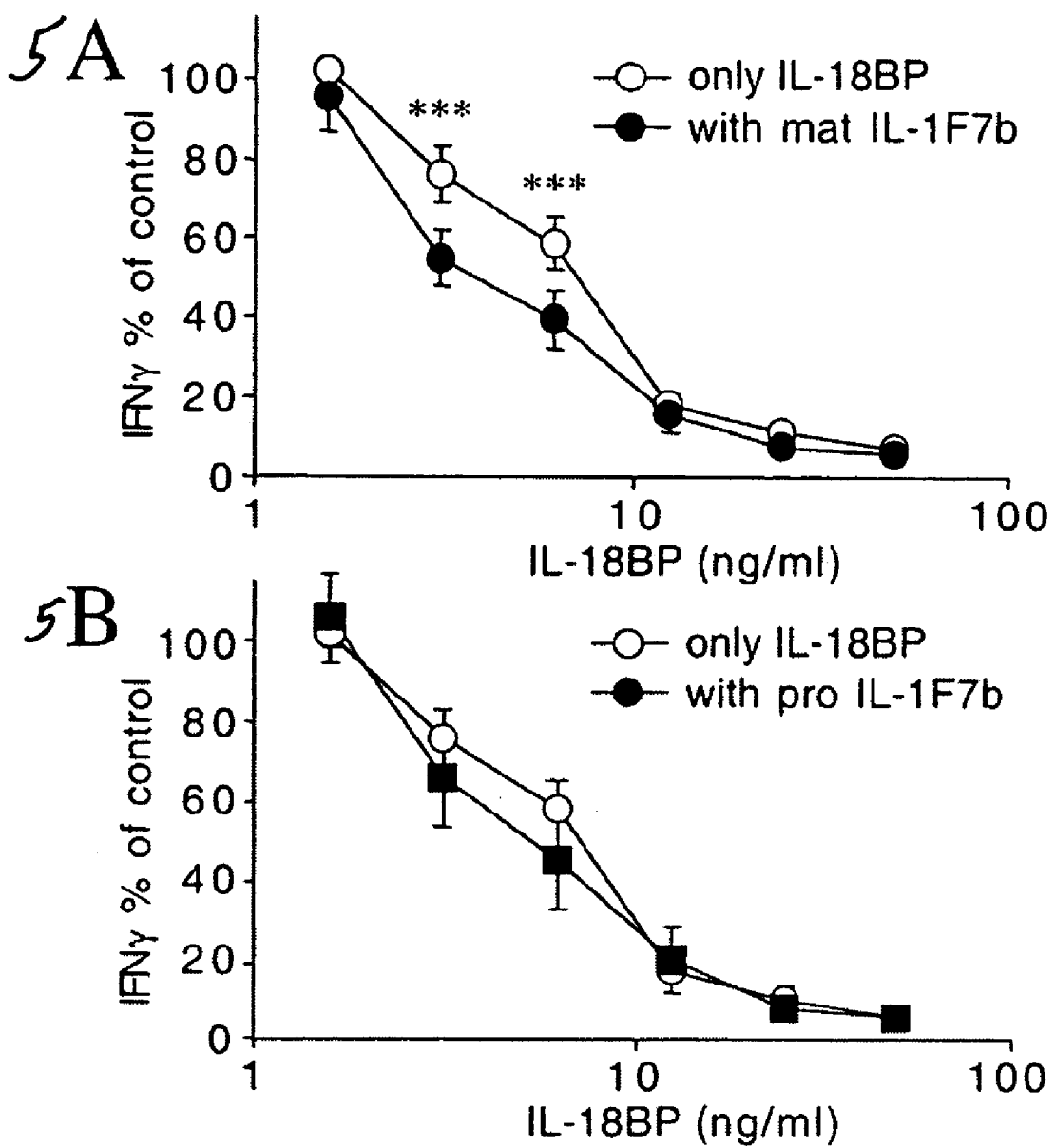

FIGS. 5A and 5B Show That IL-IF7b Enhances the Ability of IL-18BP to Inhibit the IL-18 Induced IFNγ Release by NKO Cells Mature IL-IF7b 250 ng/ml (A, 0=9) (FIG. 5A) or pro IL-IF7b (FIG. 5B) 250 ng/ml (B, 0=8), IL-18 (25 ng/ml) and a dilution of IL-18BP in RPMI/FCS 10% were incubated in 96-well microtiter plates for 1 hr prior to NKO cells (0.5× 106/ml) and IL-12 I ng/ml addition. After 16 hrs incubation with the cells, the supernatant was collected and IFNγ was measured. Values are expressed as the percentage of IFNγ-produced by NKO cells stimulated with IL-18 25 ng/ml plus IL-12 I ng/ml in the absence of IL-IF7b or IL-18BP. Statistical analysis was performed using Student's paired t-test (*** p-value<0.001).

Figure 6:
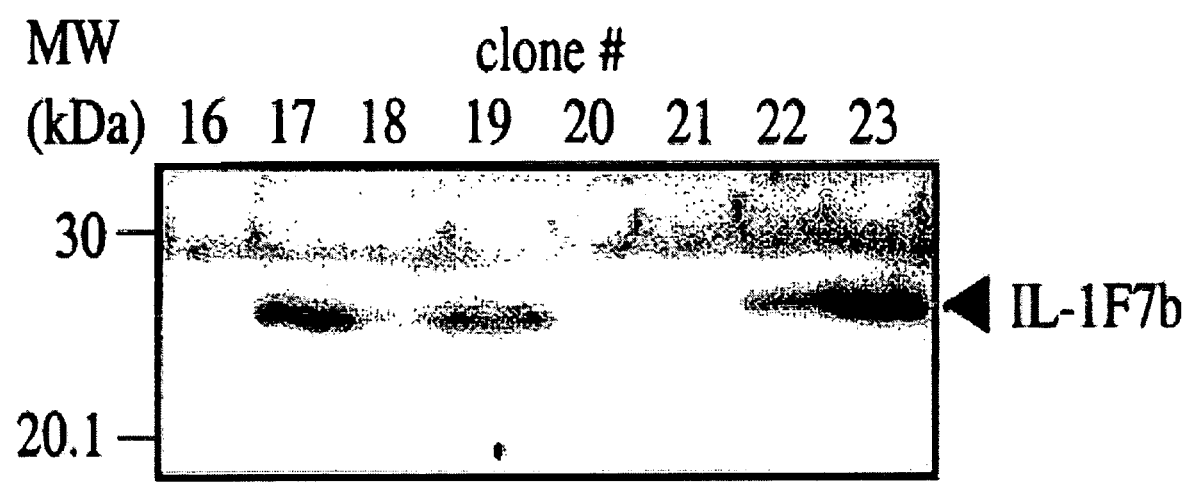

FIG. 6 Shows Expression of IL-IF7b in Transfected RAW264.7

After stable transfection, lysates of individual clones ($5 \times 10^6$ cells) were separated on SDS-PAGE and tested for IL-1F7b expression using Western blot analysis. The rabbit anti IL-1F7b serum (1:500 dilution) specifically stained IL1F7b-positive clones.

DETAILED DESCRIPTION OF THE INVENTION

The invention relates to use of a cytokine-1 (e.g. IL-1F7b) capable of binding to IL-18BP or an isoform, mutein, fused protein, functional derivative or fragment thereof and capable of inhibiting a receptor of cytokine-2, cytokine-2 being a member of the IL-1 receptor family (e.g. IL-18R), in the manufacture of a medicament for the treatment or prevention of a disease which is caused or aggravated by inducing said receptor of cytokine-2. In the present specification, the terms "inhibiting a receptor of cytokine-2" and "inhibiting the activity of a cytokine-2" are interchangeable. Thus, the invention relates to the use of a cytokine-1 capable of binding to IL-18BP or an isoform, mutein, fused protein, functional derivative or fragment thereof and capable of inhibiting the activity of a cytokine-2, being cytokine-2 member of the IL-1 family cytokines. The invention is based on the finding that IL-1F7b was shown to enhance the inhibition of IL-18 activity by IL-18BP. IL-1F7b was found to bind to IL-18BP and the complex to inhibit activation of IL-18R by IL-18, possibly, by recruiting the signalling chain of IL-18R (i.e. IL-18Rβ).

Cytokine-1, according to the invention, may be preferably a member of the IL-1 family such as IL-1F7b, IL-18, IL-1 and IL-1Ra. According to the invention, cytokine-1 and cytokine-2 are two different cytokines. For example the following combinations of cytokine-1 and 2 are selected: IL-1F7b (cytokine-1) and IL-18 (cytokine-2), IL-1F7b (cytokine-1) and IL-1 (cytokine-2), IL-18 (cytokine-1) and IL-1(cytokine-2), IL-1 (cytokine-1) and IL-18 (cytokine-2), IL-1F7b (cytokine-1) and IL-1Ra (cytokine-2), IL-1Ra (cytokine-1) and IL-18 (cytokine-2), and IL-18 (cytokine-1) and IL-1Ra (cytokine-2).

IL-1F7b (called also IL-1H4) was recently discovered as a novel member of an increasing family of proteins sharing sequence homology to IL-1 α/β, IL-1Ra and IL-18 (IL-1 family). Although IL-1F7b binds to one of the sub units of the IL-18 receptor, the IL-18Rα unit, this binding does not result in IL-18 agonistic or antagonistic function. In accordance with the present invention, by using chemical cross-linking, IL-1F7b binds IL-18Rα, but unlike IL-18, IL-1F7b fails to recruit the IL-18Rβ chain to form a functionally active, ternary complex.

The sequences of IL-1F7b and IL-18 were compared and it was found that the proteins share two conserved amino acids, i.e. amino acid E35 and K124 in IL-1F7b and E42 and K89 in IL-18. Residues E42 and K89 in IL-18 are important for both IL-18 activity and inhibition since they are involved in binding to IL-18Rα (activation) and to IL-18BP (inhibition).

In addition we found by cross linking experiments that IL-1F7b binds to IL-18BP and that in analogy to IL-18, IL-1F7b may bind to IL-18BP trough the same two conserved amino acid residues that are important for binding to IL18Rα (i.e. amino acid E35 and K124). Thus, after IL-1F7b is in a complex with IL-18BP, IL-1F7b is probably unable to bind to IL-18Rα anymore. It was found that IL-1F7b not only binds to IL-18BP but also enhances its activity i.e. enhances inhibition of IL-18 activity. This activity was found in both the precursor as well as in the mature IL-F7b protein. Since IL-1F7b in complex with IL-18BP is not able to bind to IL-18Rα, inhibition of IL-18 activity is probably caused by binding of such complex to the signalling IL-18Rβ chain. The β-chain therefore, may be recruited to the complex, depriving the β-chain to form a functional receptor complex with IL-18Rα and IL-18.

Thus, the invention embraces inhibition of signaling trough a receptor of a cytokine-2, cytokine-2 being member of a IL-1 family, by a different cytokine (cytokine-1) or an isoform, a mutein, an allelic variant or a fragment capable of binding IL18BP or an isoform, a mutein, an allelic variant or a fragment thereof.

Immunohistochemical localization studies demonstrated the presence of IL-1F7b in the monocyte population, supporting the role of IL-1F7b as a natural expressed modulator of IL-18 bioactivity.

As used herein the term "muteins" refers to analogs of a cytokine-1 such as IL-1F7b, in which one or more of the amino acid residues of cytokine-1, e.g. IL-1F7b are replaced by different amino acid residues, or are deleted, or one or more amino acid residues are added to IL-1F7b, without changing considerably the activity of the resulting products as compared with IL-1F7b. More specifically, one or more amino acids of the IL-1F7b, but no more than 30, preferably no more than 20, more preferably no more than 10, most preferably one or two amino acids, may be replaced with other amino acids, or eliminated, or may be added. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes a cytokine-1 such as IL-1F7b, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al., supra. Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SD.S at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of a cytokine-1 such as IL-1F7B, such as to have substantially similar activity to IL-1F7b. One activity of IL-1F7b is its capability of binding IL-18BP. Thus, it can be determined whether any given mutein has substantially the same activity as IL-1F7b by means of routine experimentation comprising subjecting such a mutein, e.g., to a simple sandwich competition assay to determine whether or not it binds to an appropriately labeled IL-18BP, such as radioimmunoassay or ELISA assay.

In a preferred embodiment, any such mutein has at least 40% identity or homology with the amino acid sequence of IL-1F7B. More preferably, it has at least 50%, at least 60%, at least 70%, at least 80% or, most preferably, at least 90% identity or homology thereto.

Muteins of cytokine-1 such as IL-1F7b , which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of cytokine-1 such as IL-1F7B , may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of cytokine-1 such as IL-1F7B polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising cytokine-1, preferably IL-1F7b, or a mutein or fragment thereof, fused with another protein, which, e.g., has an extended residence time in body fluids. An IL-1F7b may thus be fused to another protein, polypeptide or the like, e.g., an immunoglobulin or a fragment thereof.

"Functional derivatives" as used herein cover derivatives of cytokine-1, preferably IL-1F7bs and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-1F7B and do not confer toxic properties on compositions containing it.

These derivatives may, for example, include polyethylene glycol side-chains, which may mask antigenic sites and extend the residence of a cytokine-1, preferably IL-1F7b in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "fragments" of a cytokine-1 preferably, IL-1F7b and or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-1F7b such as binding IL-18BP and inhibiting a cytokine-2 receptor.

The invention refers also to cytokine-1 preferably to IL-IF7b isoforms, a muteins, fused proteins, functional derivatives, active fractions or circularly permutated derivatives thereof. These isoforms, muteins, fused proteins or functional derivatives retain the biological activity of cytokine-1, in particular the binding to IL18-BP, and preferably enhancement of cytokine-2 inhibition. For example the muteins of IL-1F7b retain binding capability to IL-18BP and preferably enhancement of IL-18 inhibition. The muteins retain the amino acid involved in the binding of cytokyne-1 to IL-18BP. For example, in the case of IL-1F7b the muteins retain amino acids E35 and K124. Ideally, such muteins have an enhanced biological activity as compared to unmodified cytokine-1. Preferred active fractions have an activity which is better than the activity of cytokine-1, or which have further advantages, like a better stability or a lower toxicity or immunogenicity, or they are easier to produce in large quantities, or easier to purify.

Cytokine-1, preferably IL-1F7b can be used in a pharmaceutical composition for treatment or prevention of inflammatory diseases or metastasis formation caused or aggravated by cytokine-2, preferably IL-18. It has been found that in several inflammatory diseases the level of circulating IL-18BP in patients is high, however the concentration of IL-18BP may not be sufficient in order to completely neutralize the high concentrations of IL-18 found in the circulation of such patients. Thus, administrating cytokine-1, preferably IL-1F7b, to such patients having already elevated IL-18BP, may be helpful for complete inhibition of IL-18 action. Alternatively, IL-1F7b and IL-18BP can be co-administered to patients for the treatment or prevention of inflammatory diseases selected from endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis or for the treatment or prevention of metastasis.

Since it was found that IL-1F7b, not only binds IL-18BP but it also enhances its activity (inhibition of IL-18 activity), co-administration of IL-1F7b with IL-18BP may be advantageous if administration of lower amount of IL-18BP is desired.

Cytokine-1, preferably IL-1F7b is administered in a suitable way depending on the disease. Thus it may be administered e.g. topically, systemically, subcutaneously, and intramuscularly.

Neutralization of IL-18, in animal models, revealed the important role of this cytokine in mediating inflammation (Interleukin-18, a proinflammatory cytokine. Dinarello CA. Eur Cytokine Netw September 2000; 11(3): 483-6). Thus, the invention further relates to the use of cytokine-1 or an expression vector comprising the coding sequence of the cytokine-1, preferably IL-1F7b, for the preparation of a medicament for treating or preventing inflammation. Thus, cytokine-1, preferably IL-1F7b, can be administered for the treatment or prevention of inflammatory diseases in which IL-1n 8 is known to be involved in their pathology such as endotoxin lethality (sepsis), liver injury induced by toxins or activated T cells or hepatitis C, arthritis, lung injury, psoriasis, inflammatory bowel disease, brain injury, ischemic injury, cardiac dysfunction, and neuritis.

The invention further relates to the use of an expression vector for the preparation of a medicament for preventing metastasis formation since IL-18 blockade reduces the adherence of malignant cells by preventing IL-18 upregulation of vascular endothelial adhesion-1 molecule expression. Thus, a gene therapy approach is considered in order to deliver the cytokine-1 to the site where it is required. In order to treat disorders, the gene therapy vector comprising the sequence of a cytokine-1 (e.g. IL-1F7b) may be injected directly into the diseased tissue, thus avoiding problems involved in systemic administration of gene therapy vectors, like dilution of the vectors, reaching and targeting of the target cells or tissues, and of side effects. Alternatively, the expression vector comprising the coding sequence of the cytokine-1 according to the invention can be administered by intramuscular injection.

Cytokine-1, preferably IL-1F7b and its isoforms, muteins, fused proteins, functional derivatives or active fractions as described above are the preferred active ingredients of the pharmaceutical compositions. IL-18BP and its isoforms, muteins, fused proteins, functional derivatives or active fractions as described above can be furter included as an active ingreient of the pharmaceutical compositions.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous (systemic), subcutaneous, oral, intracranial, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

Cytokine-1, preferably IL-1F7b or its isoforms, muteins, fused proteins, functional derivatives or active fractions as described above, can be used for inhibiting cytokine-2 activity in patients suffering from inflammatory diseases such as sepsis, liver injury induced by toxins or activated T cells, arthritis, lung injury, psoriasis or inflammatory bowel disease. A cytokine-1 according to the invention or its isoforms, muteins, fused proteins, functional derivatives or active fractions as described above can be also used for preventing metastasis formation, since IL-18 blockade reduces the adherence of malignant cells by preventing IL-18 upregulation of vascular endothelial adhesion-1 molecule expression. The above methods comprise the administration of a therapeutically effective amount of cytokine-1 e.g. IL-1F7b to a patient in need. cytokine-1 may be co-administered with IL-18BP or its isoforms, muteins, fused proteins, functional derivatives or active fractions as described above.

The therapeutically effective amounts of the active protein(s) will be a function of many variables, including the type of mutein, the affinity of the mutein for IL-18BP, any residual cytotoxic activity exhibited by the mutants, the route of administration, the clinical condition of the patient.

A "therapeutically effective amount" is such that when administered, a cytokine-1 such as IL-1F7b, results in enhancement of the IL-18 inhibitory activity of IL-18BP or its isoforms, muteins, fused proteins, functional derivatives or active fractions as described above. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the activity of the cytokine-1.

The use of a vector for inducing and/or enhancing the endogenous production of cytokine-1 preferably IL-1F7b, in a cell normally silent for expression of a cytokine-1, or expressing amounts of cytokine-1 which are not sufficient, are also contemplated according to the invention. The vector may comprise regulatory sequences functional in the cells desired to express the cytokine. Such regulatory sequences comprise promoters or enhancers. The regulatory sequence is then introduced into the right locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

It will be understood by the person skilled in the art that it is also possible to shut down cytokine-1 expression using the same technique, i.e. by introducing a negative regulation element, like e.g. a silencing element, into the gene locus of cytokine-1, thus leading to down-regulation or prevention of cytokine-1 expression. The person skilled in the art will understand that such down-regulation or silencing of cytokine-1 expression has the same effect as the use of a cytokine-1 inhibitor in order to prevent and/or treat disease.

Thus, when it is desired to decrease the effect of IL-18, such as in inflammatory diseases or for the inhibition of metastasis formation it would be desirable to increase the amount or the activity of cytokine-1 e.g. IL-1F7b in a cell. IL-18BP may be co-administered with cytokine-1 e.g. IL-1F7b for the treatment of subject in need.

However a decrease in the amount or the activity of cytokine-1 e.g. would be desired in situations when an enhanced IL-18 effect is sought e.g. for tumor treatment/prevention or for the treatment or prevention of a viral disease. Thus, the use of cytokine-1 and preferably IL-1F7b as a target is also contemplated according to the invention.

EXAMPLES

Example 1

The Effect of IL-1F7b on Stimulation of IFNγ Production

Based on the reported binding of IL-1F7b to the IL-18Rα chain (Pan 2001, Kumar 2002), experiments were designed to evaluate whether IL-1F7b, like IL-18, upon binding to the IL-18α receptor stimulates IFNγ production in cells. Both, the full-length molecule (pro IL-1F7b) or the mature molecule (mature IL-1F7b) using E21 as N-terminus at the predicted ICE-cleavage site (see FIG. 1), were used in the following experiments. Human NKO cells (Kim 2000), cultures of whole human blood, peripheral blood mononuclear cells (PBMC) (co-stimulated with IL-12 from Preprotech at 1 ng/ml) (PBMC for preparation see Example 8) or KG-1 cells (co-stimulated with TNFα at 10 ng/ml) (the line was obtained from ATCC Rockville, Md.), were stimulated with 100 ng/ml of recombinant IL-1F7b (pro or mature form Example 5) or IL-18. IFNγ was measured (by the liquid-phase electrochemiluminescence (ECL) in Puren 1998) in the conditioned medium of the cells 18 hours post stimulation (48 hours for KG-1). While IL-18 markedly stimulated IFNγ production (FIG. 2A), neither pro nor mature IL-1F7b stimulated any IFNy production in these cells.

Thus unlike IL18, IL-1F7b binding to IL-18Rα chain did not trigger IFNγ production i.e. binding of IL-1 F7b to the IL-18Rα chain does not recruit the IL-18Rβ chain and thus, a functionally active ternary complex is not formed.

Experiments were carried out to test whether IL-1F7b functions as an IL-18 antagonist preventing IL-18 binding to the IL-18Rα chain and consequently inhibiting its biological activity and IFNγ production. Human NK cell line was stimulated with IL-18 (20 ng/ml) in the presence of IL-12 (1 ng/ml) with increasing concentrations of pro or mature IL-1F7b and the IFNγ produced was monitored. The results obtained show no inhibition by pro or mature IL-1F7b of IL-18-induced IFNγ, even when IL-1F7b was used at a concentration of up to 40 fold molar excess over IL-18 (FIG. 2B) or when IL-1*F*7b was pre-incubated for a prolonged period with the tested cells prior to the addition of IL-18. Similar results were obtained for human PBMC (data not shown).

These results indicate that IL-1F7b neither stimulates nor inhibits IFNγ production induced by IL-18.

Example 2

Characterization of the Binding of IL-1F7b to the IL-18 Receptor

It has been reported that IL-18 binds to the IL-18Rα via the third extracellular domain (IL-18Rα: D3) (Azam 2002). In order to characterize the binding of IL-1F7b to IL-18Rα, the third extracellular domain CD3) of the IL-18Rα was individually expressed in *E. coli* as his6 tagged protein and purified via Talon-affinity chromatography. Then, IL-1F7b was incubated with such purified IL-18Rα: D3 and chemically cross-linked (Example 7). As shown in FIG. 3A, SDS-PAGE and Western blotting analysis revealed a complex of 43 kDa corresponding to cross-linked IL-1F7b and the IL-18Rα: D3. Cross-linking to IL-18Rα was observed both in pro or mature IL-1F7b. These results suggest that the IL-18Rα: D3 is crucial for binding to IL-1F7b, the very same domain that was previously demonstrated to be important for binding to IL-18.

Upon binding of IL-18 to IL-18Rα the IL-18Rβ is recruited and an active ternary complex is formed: IL-18/IL18Rα/IL-18Rβ. Thus, the following experiment was designed in order to check whether binding of IL-18Rα by IL-1F7b, similarly to IL-18, triggers a ternary complex formation: IL-1F7b/IL-18Rα/IL-18Rβ. The extracellular domains of both the IL-18Rα and IL-18Rβ were produced in Cos cells in order to ensure correct posttranslational modification such as glycosylation (Azam 2002). After incubation and chemical cross-linking of IL-18, IL-18Rα, and IL-18Rβ, a high molecular weight complex consisting of IL-18Rα, IL-18Rβ and IL-18 was observed in SDS-PAGE analysis of the cross linked proteins (FIG. 3B). However, unlike IL-18, when pro or mature IL-1F7b were incubated with IL-18Rα and IL-18Rβ such a ternary complex was not observed (FIG. 3B).

Thus, these results show that an active ternary complex is not formed upon binding of IL-1F7b to the IL-18Rα i.e. IL-18Rβ, is not recruited.

Example 3

Binding of IL-1F7b to IL-18BP

The amino acid sequence of IL-18 and IL-1F7b were compared. As shown in FIG. 1, IL-1F7b shares with IL-18 two amino acids, which are conserved in the latter, E42 and K89. E42 and K89 have been shown to be critical for the activity of IL-18 and for binding IL-18BP (Novick 1999). Thus, based on the sequence similarity of IL-1F7b with IL-18, the possibility that IL-1F7b binds to IL-18BP was investigated.

IL-1F7b (pro or mature 1.5 µg) or IL-18 (1.5 µg) were incubated in the presence or in the absence of IL-18BP and subjected to the cross-linker reagent BS3 (Example 7). Two control groups were prepared each containing the IL-18BP protein alone, one control group incubated in the presence and the other in the absence of the cross linker agent BS3. The proteins were resolved on 10% SDS-PAGE under reducing conditions and blotted on nitrocellulose. Proteins were detected on the blots using polyclonal antibodies specific to IL-1F7b or to IL-18. The results summarized in FIG. 4A show new bands that are detected only in groups containing in addition to IL-18BP pro IL-1F7b, mature IL-1F7b or IL-18 but not in the control groups. A new band of about 66 kDa which contains the pro IL-1F7b linked to IL-18BP and a new band of about 64 kDa which contains the mature IL-1F7b linked to IL-18BP (FIG. 4A) was identified on the blots.

In addition, immunoprecipitation studies were carried out with IL-1F7b (10 µg) or IL-18 (10 µg) incubated in the presence or in the absence of IL-18BP (10 µg) and crosslinked. Proteins bound and cross linked to IL-18BP were co-immunoprecipitated using monoclonal antibodies specific to IL-18BP. The immunocomplexes were resolved in a SDS-PAGE and blotted into nitrocellulose. The Blots were developed either with IL-1F7b or IL-18 specific antibodies.

The same 64 and 66 kDa bands were observed in co-precipitation studies with IL-18BP (FIG. 4B). These cross-linked band 64 and 66 kDa reflect complexes of mature IL-1F7b/IL-18BP and pro IL-1F7b/IL-18BP, respectively. These results confirmed that IL-1F7b binds to IL-18BP.

Example 4

Effect of IL-1F7b on the Inhibition of IL-18 Activity Mediated by IL-18BP

In light of the finding that IL-1F7b binds to IL-18BP (see preceding example), probably to the very same domain to which IL-18 binds, the effect of IL-1F7b on the inhibition of IL-18 activity by IL-18BP was explored. The working hypothesis was that IL-1F7b may compete with IL-18 for binding to IL-18BP, and therefore IL-18 will be less neutralized by IL-18BP in the presence of IL-1F7b.

Mature IL-1F7b 250 ng/ml or pro IL-1F7b 250 ng/ml were incubated with IL-18 (25 ng/ml) and increasing concentrations of IL-18BP (1.56-50 ng/ml) in 96-well microtiter plates for 1 hr and added together with IL-12 (1 ng/ml) to NKO cells ($0.5 \times 10^6$/ml). Following 16 hrs incubation the supernatant was collected and IFNγ was monitored (by the liquid-phase electrochemiluminescence (ECL) in ref Puren 1998).

The results show that, contrary to the hypothesis, at a low concentration of IL-18BP, the presence of IL-IF7b increased the ability of IL-18BP to inhibit IL-18-induced IFNγ (FIGS. 5A and B). At 6.25 ng/ml of IL-18BP and the presence of mature IL-1F7b, the activity of IL-18 was reduced from 76 to 55% (21% further decrease in activity). At 3.12 ng/ml of IL-18BP and the presence of mature IL-1F7b, the activity of IL-18 was reduced from 59 to 40% (19% further decrease in activity). Pro IL-1F7b was less active in this assay than mature IL-1F7b (FIG. 5B). This effect of IL-1F7b was highly reproducible and only seen at a low concentration of the IL-18BP. Similar results were obtained using PBMC (data not shown).

Example 5

Localization of IL-1F7b

IgG specific for IL-1F7b was purified from a polyclonal rabbit anti IL-1F7b serum and used to study expression of IL-1F7b in human PBMC. The specificity of the rabbit anti-IL-1F7b serum and IgG preparation was tested by two different methods using transfection of RAW264.7 macrophage cells with IL-1F7b cDNA. First, IL-1F7b antiserum specifically recognized IL-1F7b in the lysate of IL-1F7b transfected RAW264.7 cells (FIG. 6). Second, using confocal digital microscopy, affinity purified anti-IL-1F7b IgG recognised IL-1F7b expression in transfected RAW264.7 but not mock control cells (not shown). Freshly isolated human PBMC (Example 8) were stained against IL-1F7b using affinity-purified polyclonal rabbit anti-human IL-lF7b-IgG at 1 μg/ml. Using a confocal laser microscope a stacking view of a human blood monocyte expressing IL-1F7b was generated. It was observed that IL-1F7b is expressed both in the cytoplasm localized to the inner surface of the plasma membrane as well as in the nucleus (not shown). No staining of the lymphocyte population was observed.

Example 6

Protein Expression and Purification

The following oligonucleotide primers were used to clone the IL-1F7b cDNA from a human spleen library (CLONTECH® HLOOllB, BD Biosciences CLONTECH, Palo Alto, Calif.): sense primer 5'GTTGAGTAATAAACT-CAACG (SEQ ID NO: 1), reverse primer 5'GTTCAATGGGGCAGTTTC (SEQ ID NO: 2) (specific for clone AF200496 (GENBANK®) (Kumar 2000). The IL-1F7b cDNA was reamplified using a second pair of primers introducing cleavage sites for EcoRI at the 5' and XbaI at the 3' end (sense primer 5'-ATATGAATTCATGTC-CTITGTGGGGGAG (SEQ ID NO: 3); reverse primer 5'-TATATCTAGAAGTTTCCTAATCGCTGACC (SEQ ID NO: 4). Using TA-cloning the IL-1F7b cDNA was transferred into pGEM-T Easy® (Promega Corp. Medison, Wis.) according to the manufacturer's instructions and the correct sequence was verified. The IL-1F7b. cDNA was then ligated into pPROEXTMHTa (GIBCO-BRL) for bacterial expression using the EcoRI and XbaI site. The pPROEXTMHTa vector contains a N-terminal Hisx6 tag for affinity purification of the expressed protein. The pPROEXTMHTa/IL-IH4 plasmid was transformed into the competent *E. coli* strain DH5a (GIBCO-BRL). An overnight culture (10 ml) was added to 200 ml of LB medium containing 100 μg/ml ampicillin and grown until a density of 0.6-1 $OD_{600}$.

Protein expression was induced by adding isopropylthiogalactoside (0.3 mM) and incubation at 37° C. with shaking for 3 hours. Bacteria were harvested by centrifugation (5,000×g for 15 minutes at 4° C.) and the pellet was suspended in 25 ml of Talon buffer (50 mM NaH2PO4, 20 mM Tris-HCl, 100 mM NaCl, pH 8). Cells were lyzed by sonication (4×10 second bursts) on ice followed by centrifugation (4,000×g for 30 min at 4° C.). IL-1F7b was recovered from the inclusion bodies by treatment with urea 8M. The supernatant after urea treatment was cleared by centrifugation, dialyzed against Talon buffer and applied to a 2 ml mini-Talon column. The column was washed with 30 bed volumes of Talon buffer and then eluted with 5 ml of 100 mM imidazole in Talon buffer. The eluent containing affinity-purified IL-1F7b was separated using a preparative SDS-PAGE. The gel was stained with Coomassie Blue® (Bio-Rad Laboratories Inc., Hercules, Calif.) and the band containing to IL-IH4 was excised. The IL-1F7b containing gel was used to generate polyclonal sera in rabbits according to standard protocols (Rockland Inc. Gilbertsville, AP). Full length (pro) and mature IL-1F7b (N-terminus E21) used in bioassays and for cross-linking studies were produced in *E. coli* as previously described (Kumar 2002).

Example 7

Cross-linking of Proteins

Purified proteins were mixed in 30 μl of PBS and incubated for 2 hours on ice.

Then BS3 (Bis (sulfosuccininidyl) suberate) (Pierce Biotechnology Inc., Rockford, Ill.) was added to a final concentration of 1 mM and the mixture was incubated for 1 hour at RT. The reaction was quenched by the addition of Tris-CI, pH 7.4, (20 mM final concentration). After boiling for 5 min, the proteins were separated using 10% SDS-PAGE under reducing conditions (50 mM DTT) and blotted on nitrocellulose. The cross-linked proteins were detected using rabbit antisera against human IL-18BP, IL-1 F7b or IL-18 at a dilution of 1:500.

Example 8

Isolation of PBMC

PBMC were either purified from platelet-depleted residual leukocytes or from heparinized blood of healthy donors. Platelet-depleted leukocytes or whole blood was diluted 1:1 with saline and applied to FICOLL-HISTO-PAQUE® gradients (Sigma) as described previously (Kim 2001). After centrifugation, the cells from the interface were harvested, washed three times in saline and resuspended in RPMI. The isolated PBMC were kept on ice until the assay was started.

REFERENCES

The references cited below and incorporated throughout the application are incorporated herein by reference.
1. Anderson, D. M., Maraskovsky, E., Billingsley, W. L., Dougall, W. C., Tometsko, M. E., Roux, E. R., Teepe, M. C., DuBose, R. F., Cosman, D., Galibert, L. (1997) "A homologue of the TNF receptor and its ligand enhance T-cell growth and dendritic-cell function." Nature, 390, 175-179.
2. Azam, T., Novick, D., Bufler, P., Reznikov, L. L., Yoon, D. Y., Rubinstein, M. Dinarello, C. A. & Kim, S. H. (2002) J Immunol submitted.
3. Barton, J. L., Herbst, R., Bosisio, D., Higgins, L. & Nicklin, M. J. (2000) Eur J Immunol 30,3299-308.
4. Busfield, S. J., Comrack, C. A., Yu, G., Chickering, T. W., Smutko, J. S., Zhou, H., Leiby, K. R., Holmgren, L. M., Gearing, D. P. & Pan, Y. (2000) Genomics 66, 213-6.
5. Bazan, J. F., Timans, J. C. and Kaselein, R. A. (1996) "A newly defined interleukin-1?" Nature 379, 591.
6. Born, T. L., Morrison, L. A., Esteban, D. J., VandenBos, T., Thebeau, L. G., Chen, N., Spriggs, M. K., Sims, J. E., Buller, R. M. (2000) "A poxvirus protein that binds to and inactivates IL-18, and inhibits NK cell response." J Immunol 164,3246-54.
7. Corbaz et al.: J Immunol Apr. 1, 2002; 168(7):3608-16).
8. Coughlin, C. M., Salhany, K. E., Wysocka, M., Aruga, E., Kurzawa, H., Chang, A. E., Hunter, C. A., Fox, J. C., Trinchieri, G. and Lee, W. M. (1998) "Interleukin-12 and interleukin-18 synergistically induce murine tumor regression which involves inhibition of angiogenesis." J Clin Invest Mar, 101,1441-52.
9. Debets, R., Timans, J. C., Homey, B., Zurawski, S., Sana, T. R., La, S., Wagner, J., Edwards, G., Clifford, T., Menon, S., Bazan, J. F. & Kastelein, R.

A. (2001) J Immunol 167, 1440-6.
10. Desreumaux, P., Brandt, E., Gambiez, L., Emilie, D., Geboes, K., Klein, O., Ectors, N., Cortot, A., Capron, M., Colombel, J. F. (1997) Gastroenterology 113, 118-26.
11. Dinarello, C. A. (1996) BloodS7, 2095-147.
12. Dinarello "Interleukin-18, a proinflammatory cytokine." Eur Cytokine Netw September 2000; 11(3):483-6.
13. Engelmann, H., Aderka, D., Rubinstein, M., Rotman, D. and Wallach. D. (1989) "A tumor necrosis factor-binding protein purified to homogeneity from human urine protects cells from tumor necrosis factor toxicity" J. Biol. Chem. 264,11974-11980.
14. Engelmann, H., Novick, D. and Wallach, D. (1990) "Two tumor necrosis factor-binding proteins purified from human urine. Evidence for immunological cross-reactivity with cell surface tumor necrosis factor receptors." J. Biol. Chem. 265,1531-1536.
15. Ghayur, T., Banerjee, S., Hugunin, M., Butler, D., Herzog, L., Carter, A., Quintal, L., Sekut, L., Talanian, R., Paskind, M., Wong, W., Kamen, R., Tracey, D., and Allen, H. (1997) "Caspase-1 processes IFN-gamma-inducing factor and regulates LPS-induced IFN-gamma production." Nature 386, 619-623.
16. Gong, J. H., Maki, G., Klingemann, H. G. (1994) "Characterization of a human cell line (NK-92) with phenotypical and functional characteristics of activated natural killer cells." Leukemia 8:652.
17. Gu, Y., Kuida, K., Tsutsui, H., Ku, G., Hsiao, K., Fleming, M. A., Hayashi, N., Higashino, K., Okamura, H., Nakanishi, K., Kurimoto, M., Tanimoto, T., Flavell, R. A., Sato, V., Harding, M. W., Livingston, D. J., and Su, M. S. (1997) "Activation of interferon-gamma inducing factor mediated by interleukin-1beta converting enzyme." Science 275, 206-209.
18. Kaser A, Novick D, Rubinstein M, Siegmund B, Enrich B, Koch R O, Vogel W, Kim S H, Dinarwello C A, and Tilg H. Clin Exp Immunol August 2002; 129(2):332-8.
19. Kim, S. H., Eisenstein, M., Reznikov, L., Fantuzzi, G., Novick, D., Rubinstein, M. and Dinarello, C. A.(2000) "Structural requirements of six naturally occurring isoforms of the IL-18 binding protein to inhibit IL-18." Proc Natl Acad Sci USA 97, 1190-5.
20. Kohno, K., J. Kataoka, T. Ohtsuki, Y. Suemoto, I. Okamoto, M. Usui, M. Ikeda, and M. Kurimoto. (1997) "IFN-gamma-inducing factor (IGIF) is a costimulatory factor on the activation of Th1 but not Th2 cells and exerts its effect independently of IL-12." J. Immunol. 158:1541-1550.
21. Kumar, S., McDonnell, P. C., Lehr, R., Tierney, L., Tzimas, M. N., Griswold, D. E. Capper, E. A., Tal-Singer, R., Wells, G. I., Doyle, M. L. & Young, P. R. (2000) J Biol Chern 275, 10308-14.
22. Lin, H., Ho, A. S., Haley-Vicente, D., Zhang, J., Bemal-Fussell, J., Pace, A. M., Hansen, D., Schweighofer, K., Mize, N. K. & Ford, J. E. (2001) J Bioi Chern 276, 20597-602.
23. Mallat, Silvestre J, Le Ricoussanne S, Lecomte-Raclet L, Corbaz A, Clergue M, Duriez M, Barateau V, Akira S, Tedgui A, Tobelem G, Chvatchko Y and Levy B I. (2002) Circ Res. 91 (5), 441-8.
24. Matsumoto, S., Tsuji-Takayamu, K., Aizawa, Y., Koide, K., Takeuchi, M., Ohta, T., Kurimoto, M. (1997) Biochem. Biophys. Res. Commun. 234, 454-7.
25. Monteleone, G., Trapasso, F., Parrello, T., Biancone, L., Stella, A., Juliano, R., Luzza, F., Fusco, A., Pallone, F. (1999) J. Immunol. 163, 143-7.
26. Mulero, J. J., Pace, A. M., Nelken, S. T., Loeb, D. B., Correa, T. R., Drrnanac, R. & Ford, J. E. (1 999) Biochem Biophys Res Commun 263, 702-6.
27. Nakanishi, K., Yoshimoto, T., Tsutsui, H. & Okamura, H. (2001) Annu Rev Immunol19, 423-74.
28. Nakamura, K., Okamura, H., Wada, M., Nagata, K. and Tamura, T. (1989). "Endotoxin-induced serum factor that stimulates gamma interferon production." Infect-Immun 57,590-5 issn: 0019-9567.
29. Nakamura, K., Okamura, H., Nagata, K., Komatsu, T. and Tamura, T. (1993) "Purification of a factor which provides a costimulatory signal for gamma interferon production." Infect. Immun. 61, 64-70.
30. Novick, D., Engelmann, H., Wallach, D. and Rubinstein. M. (1989) "Soluble cytokine receptors are present in normal human urine." J. Exp. Med. 170,1409-14.
31. Novick, D., Cohen, B. and Rubinstein, M. (1992) "Soluble Interferon-alpha Receptor Molecules Are Present in Body Fluids." FEBS Lett 314,445-8.
32. Novick, D., Cohen, B. and Rubinstein, M. (1994) "The Human Interferon alpha/beta Receptor—Characterization and Molecular Cloning." Cell 77,391-400.
33. Novick, D., Kim, S., Fantuzzi, G., Reznikov, L. L., Dinarello, C. A. and Rubinstein, M. (1999) "Interleukin-18 Binding Protein: A Novel Modulator of the Th1 Cytokine Response. Immunity 10, 127,36.
34. Novick, D., Schwartsburd, B., Pinkus, R., Suissa, D., Belzer, I., Sthoeger, Z., Keane, W. F., Chvatchko, Y., Kim, S. H., Fantuzzi, G., Dinarello, C. A. & Rubinstein, M. (2001) Cytokine 14, 334-42.
35. Ohta Y, Hamada Y, Katsuoka K. Arch Dermatol Res July 2001; 293(7):334-42
36. Okamura, H., Tsutsui, H., Komatsu, T., Yutsudo, M., Hakura, A., Tanimoto, T., Torigoe, K., Okura, T., Nukada, Y., Hattori, K., Akita, K., Namba, M., Tanabe, F., Konishi, K., Fukuda, S., and Kurimoto, M. (1995) "Cloning of a new cytokine that induces IFN-gamma production by T cells." Nature 378, 88-91.
37. Pan, G., Risser, P., Mao, W., Baldwin, D. T., Zhong, A. W., Filvaroff, E., Yansura, D., Lewis, L., Eigenbrot, C., Henzel, W. J. & Vandlen, R. (2001) Cytokine 13, 1-7.
38. Pizarro, T. T., Michie, M. H., Bentz, M., Woraratanadharm, J., Smith, M. F., Foley, E., Moskaluk, C. A., Bickston, S. J., Cominelli, F. (1999) J. Immunol. 162, 6829-35.
39. Puren, A. J., Fantuzzi, G., Gu, Y., Su, M. S. & Dinarello, C. A. (1998) J Clin Invest 101, 711-21.
40. Puren, A. J., Razeghi, P., Fantuzzi, G. & Dinarello, C. A. (1998) J Infect Dis 178, 1830-4.
41. Puren, A. J., Fantuzzi, G., Dinarello, C. A. (1999) Proc Natl Acad Sci USA 96,2256-61.
42. Raebum C D, Dinarello C A, Zimmerman M A, Calkins C M, Pomerantz B J, McIntyre R C Jr, Harken A H and Meng X. (2002) AM J PHYSIOL HEART CIRC PHYSIOL 283(2), H650-7.
43. Reimund, J. M., Wittersheim, C., Dumont, S., Muller, C. D., Kenney, J. S., Baumann, R., Poindron, P., Duclos, B. (1996) Gut 39, 684-9.
44. Seki, S., Habu, Y., Kawamura, T., Takeda, K., Dobashi, H., Ohkawa, T., Hiraide, H. (2000) "The liver as a crucial organ in the first line of host defense: the roles of Kupffer cells, natural killer (NK) cells and NK1.1 Ag+T cells in T helper 1 immune responses." Immunol Rev 174,35-46.
45. Simonet, W. S., Lacey, D. L., Dunstan, C. R., Kelley, M., Chang, M. S., Luthy, R., Nguyen, H. Q., Wooden, S., Bennett, L., Boone, T., Shimamoto, G., DeRose, M., Elliott, R., Colombero, A., Tan, H. L., Trail, G., Sullivan, J., Davy, E., Bucay, N., Renshaw-Gegg, L., Hughes, T. M., Hill, D., Pattison, W., Campbell, P., Boyle, W. J. (1997). "Osteoprotegerin: a novel secreted protein involved in the regulation of bone density". Cell, 89, 309-19.
46. Smith, D. E., Renshaw, B. R., Ketchem, R. R., Kubin, M., Garka, K. E. & Sims, J. E. (2000) J Biol Chern 275, 1169-75.
47. Tasaki et al (2000) Cancer Gene Ther (2):247-54.Tsutsui, H., K. Nakanishi, K. Matsui, K. Higashino, H. Okamura, Y. Miyazawa, and K. Kaneda. (1996) "IFN-gamma-inducing factor up-regulates Fas ligand-mediated cytotoxic activity of murine natural killer cell clones". J. Immunol. 157,3967-73 issn: 0022-1767.
48. Urushihara, N., Iwagaki, H., Yagi, T., Kohka, H., Kobashi, K., Morimoto, Y., Yoshino, T., Tanimoto, T., Kurimoto, M., Tanaka, N. (2000) "Elevation of serum interleukin-18 levels and activation of Kupffer cells in biliary atresia." J Pediatr Surg 35,446-9.
49. Ushio, S., Namba, M., Okura, T., Hattori, K., Nukada, Y., Akita, K., Tanabe, F., Konishi, K., Micallef, M., Fujii, M., Torigoe, K., Tanimoto, T., Fukuda, S., Ikeda, M., Okamura, H., and Kurimoto, M. (1996) J. Immunol. 156, 4274-9
50. Vigers, G. P., Anderson, L. J., Caffes, P., Brandhuber, B. J. (1997) "Crystal structure of the type-I interleukin-1 receptor complexed with interleukin-1beta." Nature 386, 190-4.
51. Xiang, Y. and Moss, B.(1999) "IL-18 binding and inhibition of interferon gamma induction by human poxvirus-encoded proteins." Proc Natl Acad Sci USA 96,11537-42.
52. Yasuda, H., Shima, N., Nakagawa, N., Mochizuki, S. I., Yano, K., Fujise, N., Sato, Y., Goto, M., Yamaguchi, K., Kuriyama, M., Kanno, T., Murakami, A., Tsuda, E., Morinaga, T., Higashio, K. (1998) "Identity of osteoclastogenesis inhibitory factor (OCIF) and osteoprotegerin (OPG): a mechanism by which OPG/OCIF inhibits osteoclastogenesis in vitro." Endocrinology, 139, 1329-37.
53. Yatsiv I, Morganti-Kossmann M C, Perez D, Dinarello C A, Novick D, Rubinstein M, Otto V I, Rancan M, Kossmann T, Redaelli C A, Trentz O, Shohami E, and Stahel P F. J Cereb Blood Metab August 2002; 22(8):971-8.
54. Yu S, Chen Z, Mix E, Zhu S W, Winbald B, Ljunggren H G, Zhu J. J Neuropathol Exp Neurol 2002; 61 (7):614-22.
55. Zecchina et al J Hematother Stem Cell Res 2001.

The invention claimed is:

1. A method of treating or inhibiting rheumatoid arthritis, ulcerative colitis, or Crohn's disease in a patient in need thereof, the method comprising administration of an effective amount of IL-1F7B to bind to IL-18R, wherein the IL-1F7b is administered together with an effective amount of IL-18BP.

2. The method of claim 1, wherein the IL-1F7B binds to the signaling chain of IL-18R.

3. The method of claim 1, wherein the IL-1F7B is administered systemically, subcutaneously, or intramuscularly.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttgagtaat aaactcaacg                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttcaatggg gcagtttc                                                18

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatgaattc atgtccttgt gggggag                                      27

<210> SEQ ID NO 4
<211> LENGTH: 29
<212> TYPE: DNA
<213> ORGANISM: Artificial Sequence

```
<220> FEATURE:
<223> OTHER INFORMATION: Description of Artificial Sequence: Synthetic
       primer

<400> SEQUENCE: 4
tatatctaga agtttcctaa tcgctgacc                                              29

<210> SEQ ID NO 5
<211> LENGTH: 193
<212> TYPE: PRT
<213> ORGANISM: Homo sapiens

<400> SEQUENCE: 5
```

Met Ala Ala Glu Pro Val Glu Asp Asn Cys Ile Asn Phe Val Ala Met
 1               5                  10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

```
<210> SEQ ID NO 6
<211> LENGTH: 218
<212> TYPE: PRT
<213> ORGANISM: Homo sapiens

<400> SEQUENCE: 6
```

Met Ser Phe Val Gly Glu Asn Ser Gly Val Lys Met Gly Ser Glu Asp
 1               5                  10                  15

Trp Glu Lys Asp Glu Pro Gln Cys Cys Leu Glu Asp Pro Ala Val Ser
            20                  25                  30

Pro Leu Glu Pro Gly Pro Ser Leu Pro Ala Met Asn Phe Val His Thr
        35                  40                  45

Ser Pro Lys Val Lys Asn Leu Asn Pro Lys Lys Phe Ser Ile His Asp
    50                  55                  60

Gln Asp His Lys Val Leu Val Leu Asp Ser Gly Asn Leu Ile Ala Val
65                  70                  75                  80

Pro Asp Lys Asn Tyr Ile Arg Pro Glu Ile Phe Phe Ala Leu Ala Ser
                85                  90                  95

```
Ser Leu Ser Ser Ala Ser Ala Glu Lys Gly Ser Pro Ile Leu Leu Gly
            100             105             110

Val Ser Lys Gly Glu Phe Cys Leu Tyr Cys Asp Lys Asp Lys Gly Gln
            115             120             125

Ser His Pro Ser Leu Gln Leu Lys Lys Glu Lys Leu Met Lys Leu Ala
    130             135             140

Ala Gln Lys Glu Ser Ala Arg Arg Pro Phe Ile Phe Tyr Arg Ala Gln
145             150             155             160

Val Gly Ser Trp Asn Met Leu Glu Ser Ala Ala His Pro Gly Trp Phe
                165             170             175

Ile Cys Thr Ser Cys Asn Cys Asn Glu Pro Val Gly Val Thr Asp Lys
            180             185             190

Phe Glu Asn Arg Lys His Ile Glu Phe Ser Phe Gln Pro Val Cys Lys
            195             200             205

Ala Glu Met Ser Pro Ser Glu Val Ser Asp
    210             215
```